United States Patent
Dai et al.

(10) Patent No.: US 11,180,763 B2
(45) Date of Patent: Nov. 23, 2021

(54) CRISPR/CAS9 VECTOR COMBINATION AND APPLICATION THEREOF IN GENE KNOCKOUT

(71) Applicant: NANJING GENEFRIEND-BIOTECH INC., Jiangsu (CN)

(72) Inventors: Yifan Dai, Jiangsu (CN); Haiyuan Yang, Jiangsu (CN); Ying Wang, Jiangsu (CN)

(73) Assignee: Nanjing Genefriend-Biotech Inc., Jiangsu (CN)

(*) Notice: Subject to any disclaimer, the term of this patent is extended or adjusted under 35 U.S.C. 154(b) by 0 days.

(21) Appl. No.: 16/968,664

(22) PCT Filed: Mar. 14, 2019

(86) PCT No.: PCT/CN2019/078060
§ 371 (c)(1),
(2) Date: Aug. 10, 2020

(87) PCT Pub. No.: WO2019/154437
PCT Pub. Date: Aug. 15, 2019

(65) Prior Publication Data
US 2021/0002652 A1  Jan. 7, 2021

(30) Foreign Application Priority Data
Feb. 11, 2018 (CN) .......................... 201810139547.8

(51) Int. Cl.
| | | |
|---|---|---|
| *C12N 15/66* | (2006.01) | |
| *A01K 67/027* | (2006.01) | |
| *C12N 9/22* | (2006.01) | |
| *C12N 15/877* | (2010.01) | |
| *C12N 15/90* | (2006.01) | |

(52) U.S. Cl.
CPC .......... *C12N 15/66* (2013.01); *A01K 67/0276* (2013.01); *C12N 9/22* (2013.01); *C12N 15/8778* (2013.01); *C12N 15/907* (2013.01); *A01K 2217/075* (2013.01); *A01K 2227/108* (2013.01); *C12N 2310/20* (2017.05); *C12N 2320/31* (2013.01); *C12Y 114/18002* (2013.01); *C12Y 204/01087* (2013.01)

(58) Field of Classification Search
None
See application file for complete search history.

(56) References Cited

U.S. PATENT DOCUMENTS

| | | | |
|---|---|---|---|
| 2016/0165861 A1* | 6/2016 | Hering | C07K 16/2866 800/14 |
| 2017/0311579 A1* | 11/2017 | Tector, III | A61K 35/407 |

FOREIGN PATENT DOCUMENTS

| | | |
|---|---|---|
| CN | 101386650 A | 3/2009 |
| CN | 105518135 A | 4/2016 |
| CN | 107034237 A | 4/2016 |
| CN | 108220294 A | 6/2018 |
| WO | 2017104404 A1 | 6/2017 |

OTHER PUBLICATIONS

PCT/CN2019/078060 International Search Report dated Jun. 11, 2019.

* cited by examiner

*Primary Examiner* — Christopher M Babic
*Assistant Examiner* — Kimberly A Aron
(74) *Attorney, Agent, or Firm* — Honigman LLP; Thomas A. Wootton, Esq.; Jonathan P. O'Brien

(57) ABSTRACT

Provided is an SgRNA combination, comprising an SgRNA specifically targeting the GGTA1 gene, an SgRNA specifically targeting the CMAH gene and an SgRNA specifically targeting the β4GalNT2 gene. Also provided is a CRISPR/Cas9 vector combination, comprising a GGTA1-CRISPR/Cas9 vector, a CMAH-CRISPR/Cas9 vector and a β4GalNT2-CRISPR/Cas9 vector. Also provided is an applicaton of the CRISPR/Cas9 vector combination in knocking out the GGTA1 gene, the CMAH gene and the β4GalNT2 gene. The knockout rates of the three genes with the specifically targeted SgRNA sequences are respectively 56%, 63%, and 41%. A three genes knockoutpig can be obtained, wherein the three genes related to immune rejectionare knocked out, and heart valves of said pig can be acquired.

8 Claims, 4 Drawing Sheets
Specification includes a Sequence Listing.

CRISPR/CAS9 VECTOR COMBINATION AND APPLICATION THEREOF IN GENE KNOCKOUT

CROSS-REFERENCE TO RELATED APPLICATIONS

This application is a National Stage Application and claims priority under 35 U.S.C. § 371 to Patent Cooperation Treaty application PCT/CN2019/078060, filed Mar. 14, 2019, which claims the benefit of CN 201810139547.8, filed Feb. 11, 2018, priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety and includes the Sequence Listing entitled "262790-464745_2020-08-10_Seq_Listing_ST25.txt", is 34,456 bytes in size and was created on Aug. 10, 2020, and filed electronically herewith.

TECHNICAL FIELD

The present invention relates to the technical field of gene engineering, specifically to a CRISPR/Cas9 vector and a use thereof in gene knockout.

BACKGROUND

At present, mechanical artificial heart valves or glutaraldehyde-fixed wild-type heart valves from pig or bovine tissue (referred to as GBHV) are clinically used for cardiac replacement therapy. Although they have been applied clinically, some problems leading to poor transplantation effect still exist. First, glutaraldehyde fixation will inactivate vascular endothelial cells, and damage the transplantation effect; second, the calcification of GBHV will cause structural valve degeneration, and patients have to undergo a further operation, thereby increasing the morbidity and mortality; third, studies have shown that 90% of people over 65 maintain a GBHV transplantation success for more than 10 years, while only 18% of adolescents maintain a transplantation success for 3 years. A reason causing the significant difference in transplantation results of people at different ages is that young people wear out quickly, have a stronger immune system, and exhibit more obvious reject reaction. A main factor leading to calcification and structural valve degeneration is an antibody-mediated immune reject reaction.

α-1,3-Galactosyltransferase (GGTA1), CMP-N-acetylneuraminic acid hydroxylase (CMAH) and β-1,4-N-acetyl galactosaminyl transferase 2 (β4GalNT2) which are abundantly expressed in porcine organs and tissues are three types of primary antigens causing xenotransplantation immune reject reaction (Estrada, J. L., et al., Evaluation of human and non-human primate antibody binding to pig cells lacking GGTA1/CMAH/beta4GalNT2 genes. Xenotransplantation, 2015. 22(3): p. 194-202).

SUMMARY

Invention objects: To address the antibody-mediated immune reject reaction occurred in the existing cardiac replacement therapy, the present invention provides a GGTA1/CMAH/β4GalNT2-CRISPR/Cas9 vector, and a further object of the present invention is to provide a use of the GGTA1/CMAH/β4GalNT2-CRISPR/Cas9 vector in the knockout of GGTA1/CMAH/β4GalNT2 gene.

Technical Solutions: An SgRNA combination of the present invention, comprising an SgRNA specifically targeting a GGTA1 gene, an SgRNA specifically targeting a CMAH gene and an SgRNA specifically targeting a β4GalNT2 gene, wherein said SgRNA specifically targeting a GGTA1 gene comprising a nucleotide sequence as set forth in SEQ ID No:1, said SgRNA specifically targeting a CMAH gene comprising a nucleotide sequence as set forth in SEQ ID No:2, and said SgRNA specifically targeting a β4GalNT2 gene comprising a nucleotide sequence as set forth in SEQ ID No:3.

A further object of the present invention is to provide a CRISPR/Cas9 vector combination comprising a GGTA1-CRISPR/Cas9 vector, a CMAH-CRISPR/Cas9 vector and a β4GalNT2-CRISPR/Cas9 vector; wherein said GGTA1-CRISPR/Cas9 vector comprising a nucleotide sequence as set forth in SEQ ID No:1, said CMAH-CRISPR/Cas9 vector comprising a nucleotide sequence as set forth in SEQ ID No:2, and said β4GalNT2-CRISPR/Cas9 vector comprising a nucleotide sequence as set forth in SEQ ID No:3.

Said GGTA1-CRISPR/Cas9 vector has a nucleotide sequence as represented by SEQ ID No:4; said CMAH-CRISPR/Cas9 vector has a nucleotide sequence as represented by SEQ ID No:5; and said β4GalNT2-CRISPR/Cas9 vector has a nucleotide sequence as represented by SEQ ID No:6.

Said CRISPR/Cas9 vector is constructed through the following method:

(1) digesting a pX330 plasmid with a restriction enzyme, isolating the digested plasmid with an agarose gel, followed by purifying and recovering the digested product with a gel extraction kit;

(2) annealing the SgRNA sequence in accordance with the following procedures: 37° C. 30 min 95° C. 5 min, and then cooling to 25° C. at a rate of 5° C./min;

(3) linking the digested product obtained in step (1) to the SgRNA sequence annealed in step (2) with a ligase;

(4) treating the system obtained in step (3) with a plasmid-safe exonuclease to remove the improperly linked plasmid;

(5) transforming the plasmid into a competent cell for culture; and (6) extracting the plasmid from the competent cell cultured in step (5) for sequencing, thereby determining successful construction of the vector.

When said CRISPR/Cas9 vector is a GGTA1-CRISPR/Cas9 vector, said SgRNA nucleotide sequence in step (2) is set forth in SEQ ID No:1; when said CRISPR/Cas9 vector is a CMAH-CRISPR/Cas9, said SgRNA nucleotide sequence in step (2) is set forth in SEQ ID No:2; and when said CRISPR/Cas9 vector is a β4GalNT2-CRISPR/Cas9 vector, said SgRNA nucleotide sequence in step (2) is set forth inSEQ ID No:3.

A further object of the present invention is to provide a use of said CRISPR/Cas9 vector combination in knockout of GGTA1 gene, CMAH gene and β4GalNT2 gene,comprising the following steps:

(1) transforming the CRISPR/Cas9 vector combination into a porcine fetal fibroblast; and (2) performing a resistance screening on the fibroblast obtained in step (1) with G418 antibiotics, followed by subjecting the fibroblast having resistance to PCR amplification gene sequencing, thereby obtaining the fibroblasts with the GGTA1 gene, CMAH gene and β4GalNT2 gene knocked out.

A further object of the present invention is to provide a use of said CRISPR/Cas9 vector combination in preparation of the heart valve of a pig with the GGTA1 gene, CMAH gene and β4GalNT2 gene knocked out, comprising the following steps:

(1) transforming the CRISPR/Cas9 vector combination into a porcine fetal fibroblast;

(2) performing a resistance screening on the fibroblast obtained in step (1) with G418 antibiotics, followed by subjecting the fibroblast having resistance to PCR amplification gene sequencing, thereby obtaining the fibroblasts with the GGTA1 gene, CMAH gene and β4GalNT2 gene knocked out;

(3) transplanting the nucleus of the fibroblast obtained in step (2) into an enucleated porcine oocytes for culturing to blastocyst stage;

(4) transplanting the blastocyst obtained in step (3) into a surrogate porcine for feeding and parturition; and (5) extracting the genome of the porcine obtained in step (4), followed by amplification with a PCR primer for genotype identification.

A further object of the present invention is to provide a use of said sgRNA combination in preparation of a kit for GGTA1 gene, CMAH gene and β4GalNT2 gene knockout.

Beneficial effects: (1) By designing an SgRNA sequence including specifically targeting GGTA1 gene, CMAH gene and targeting β4GalNT2 gene, the knockout effects of the three genes are 56%, 63% and 41%, respectively;

(2) by modifying the gene of porcine, knocking out three genes (GGTA1/CMAH/β4GalNT2) associated with the immune reject reaction in a manner of frameshift mutation, it can completely knock out the aforesaid three genes, obtain three-knockout porcine and obtain its heart valve; and (3) the heart valve of three-knockout porcine exhibits a significantly decreased binding with immunoglobulin in human serum, and produces a significant effect on overcoming a hyperacute immune reject reaction, and effectively solves the problems of xenotransplanted organ shortage and calcification, as well as structural valve degeneration. It has become a source of new materials for GBHV, laid the foundation for gene modification of xenotransplanted organ donors, and provided a valuable source of material for clinical cardiac replacement therapy.

DETAILED DESCRIPTION OF THE EMBODIMENTS

Example 1

Construction of CRISPR/Cas9 Vector

First, an SgRNA (single guide RNA) targeting GGTA1, CMAH and β4GalNT2 gene was synthesized in accordance with the DNA sequence of GGTA1/CMAH/β4GalNT2 gene, and a GGTA1-CRISPR/Cas9 vector, a CMAH-CRISPR/Cas9 vector and a β4GalNT2-CRISPR/Cas9 vector were respectively constructed by use of pX330 as a skeleton plasmid.

Figure 1:
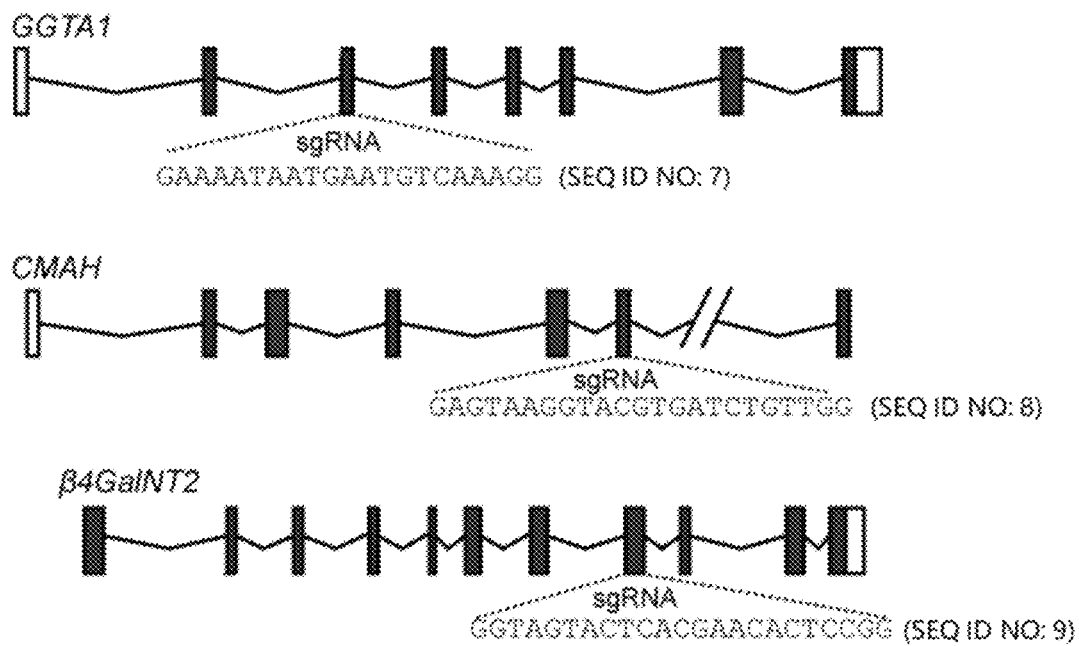
FIG. 1 is a schematic diagram of CRISPR/Cas9 targets of GGTA1, CMAH and β4GalNT2 genes, wherein the nucleic acid of sgRNA targeting GGTA1 is as set forth in SE ID NO: 7, the nucleic acid of sgRNA targeting CMAH is as set forth in SEQ ID NO: 8, and the nucleic acid of sgRNA targeting β4GalNT2 1 is as set forth in SEQ ID NO: 9.

I. The GGTA1-CRISPR/Cas9 vector was constructed through the following method:

First, in accordance with the porcine GGTA1 gene sequence disclosed by Genbank, the exon3 of the GGTA1 gene was selected as the CRISPR/Cas9 target. In accordance with the design principles of cas9 target: the 5' end was G, the 3'end was a PAM sequence (NGG), the SgRNA sequence was designed as GAAAATAATGAATGTCAA, as shown in FIG. 1, the nucleotide sequence is set forth in SEQ ID No:1.

The GGTA1-CRISPR/Cas9 vector was constructed through the following method:

Step (1), in accordance with the design principles of cas9 target that the 5' end was G and the 3' end was a PAM sequence (NGG), finding the targeting site in the GGTA1 gene;

Step (2), purchasing a pX330 skeleton plasmid expressing hSpCas9 and gRNA (Addgene plasmid 423230); and Step (3), synthesizing the 5'-end phosphorylated oligonucleotide chain SgRNA sequence GAAAATAAT-GAATGTCAA (SEQ ID NO: 1) by the company.

The SgRNA sequence was cloned into the pX330 skeleton vector in the following specific steps:

1. Digesting 1ug of pX330 plasmid with a restriction enzyme BbsI;

2. Isolating the digested pX330 plasmid by an agarose gel (an agarose gel at a concentration of 1%, i.e., 1 g of agarose gel was added into 100 mL of electrophoresis buffer), followed by purifying and recovering the digested product with a gel extraction kit (QIAGEN);

3. Annealing the synthesized 5'end phosphorylated oligonucleotide chain SgRNA sequence in accordance with the following procedures:

37° C. 30 min

95° C. 5 min, and then cooling to 25° C. at a rate of 5° C./min.

4. Initiating a linking reaction in accordance with the following system: Reaction at room temperature for 10 min The BbsI-digested pX330 obtained in step 2 50 ng
The annealed 5'end phosphorylated oligonucleotide obtained in step 3 (1:250 v/v, diluted with sterile water) 1 μL
2× flashlinking buffer (NEB) 5 μL
Diluting the system to 10 μL with ddH$_2$O
Sub-total 10 μL
Flash ligase (NEB) 1 μL
Total 11 μL 5. Treating the linking system with a plasmid-safe exonuclease to remove the improperly linked plasmid:

The linking reaction system obtained in step 4 11 μL
10× plasmid-safe buffer (NEB) 1.5 μL
10 mM ATP 1.5 μL
Plasmid-safe exonuclease (NEB) 1 μL
Total 15 μL
Reaction at 37° C. for 30 min 6. Transforming (1) 50 μL of competent cells (TIANGEN) were placed in an ice bath;

(2) 15 μL of a solution free of improperly linked plasmid obtained in step 5 was added into a centrifuge tube containing competent cells, and then stood in the ice bath for 30 min after uniformly mixed;

(3) The competent cells ice-cooled for 30 min were placed in a water bath at 42° C. for 60-90 s, and then rapidly transferred into the ice bath, allowing the cells to cool for 2-3 min;

(4) 900 μL of sterile LB medium (free of antibiotics) was added into the centrifuge tube, and placed on a 37° C. shaker for shaking culture at 150 rpm for 45 min after uniformly mixed; and (5) The centrifuge tube was placed in a centrifuge to undergo a centrifugation at 12000 rpm for 5 min, and then 900 μL of supernatant was discarded, and the precipitates of competent cells were re-suspended in the residual 100 μL of supernatant, the re-suspended competent cells were added onto an LB solid agar medium containing the corresponding antibiotic, uniformly spread with a sterile spreading rod; and the LB solid agar medium coated with the competent cells was incubated by reversion in a 37° C. incubator for 12-16 h.

7. Carefully extracting the plasmid, sequencing by the company, and identifying for the successful construction of the targeting plasmid.

The constructed CRSAPR/Cas9 vector is designated as GGTA1-PX330, with a full nucleotide sequence as set forth in SEQ ID No:4.

II. CMAH-CRISPR/Cas9 Vector was Constructed through the Following Method:

First, in accordance with the porcine CMAH gene sequence disclosed by Genbank, exon6 of the CMAH gene was selected as the CRISPR/Cas9 target. In accordance with the design principles of cas9 target: 5'end was G, 3'end was a PAM sequence (NGG), the SgRNA guide sequence was designed as GAGTAAGGTACGTGATCTGT, as shown in FIG. 1, the nucleotide sequence was set forth in SEQ ID No:2.

The CMAH-CRISPR/Cas9 vector was constructed through the following method:

Step (1), in accordance with the design principles of cas9 target that 5' end was G and 3' end was a PAM sequence (NGG), finding the targeting site in the CMAH gene;

Step (2), purchasing a pX330 skeleton plasmid expressing hSpCas9 and gRNA (Addgene plasmid 423230); and Step (3), synthesizing the 5' end phosphorylated oligonucleotide chain SgRNA sequence GAGTAAGGTACGT-GATCTGT (SEQ ID NO: 2) by the company.

The SgRNA sequence was cloned into the pX330 skeleton vector in the following specific steps:

1. Digesting lug of pX330 plasmid with a restriction enzyme BbsI;

2. Isolating the digested pX330 plasmid by an agarose gel (an agarose gel at a concentration of 1%, i.e., 1 g of an agarose gel was added into a 100 mL electrophoresis buffer), followed by purifying and recovering the digested product with a gel extraction kit (QIAGEN);

3. Annealing the synthesized 5'end phosphorylated oligonucleotide chain SgRNA sequence in accordance with the following procedures:
37° C. 30 min
95° C. 5 min, and then cooling to 25° C. at a rate of 5° C./min.

4. Initiating a linking reaction in accordance with the following system: Reaction at room temperature for 10 min The BbsI-digested pX330 obtained in step 2 50 ng
The annealed 5'end phosphorylated oligonucleotide obtained in step 3 (1:250 v/v, diluted with sterile water) 1 μL
2× flashlinking buffer (NEB) 5 μL
Diluting the system to 10 μL with ddH$_2$O
Sub-total 10 μL
Flash ligase (NEB) 1 μL
Total 11 μL 5. Treating the linking system with a plasmid-safe exonuclease to remove the improperly linked plasmid:

The linking reaction system obtained in step 4 11 μL
10× plasmid-safe buffer (NEB) 1.5 μL
10 mM ATP 1.5 μL
Plasmid-safe exonuclease (NEB) 1 μL
Total 15 μL
Reaction at 37° C. for 30 min 6. Transforming (1) 50 μL of competent cells (TIANGEN) were placed in an ice bath;

(2) 15 μL of a solution free of the improperly linked plasmid obtained in step 5 was added to a centrifuge tube containing the competent cells, and stood in the ice bath for 30 min after uniformly mixed;

(3) The competent cells ice-cooled for 30 min were placed in a water bath at 42° C. for 60-90 s, and then rapidly transferred into the ice bath, allowing the cells to cool for 2-3 min;

(4) 900 μL of a sterile LB medium (free of antibiotics) was added into the centrifuge tube, and placed on a 37° C. shaker for shaking culture at 150 rpm for 45 min after uniformly mixed; and (5) The centrifuge tube was placed in a centrifuge to undergo a centrifugation at 12000 rpm for 5 min, and then 900 μL of supernatant was discarded, and the precipitates of competent cells were re-suspended in the residual 100 uL of supernatant,the re-suspended competent cells were added onto an LB solid agar medium containing the corresponding antibiotic, uniformly spread with a sterile spreading rod; and the LB solid agar medium coated with the competent cells was incubated by reversion in a 37° C. incubator for 12-16 h.

7. Carefully extracting the plasmid, sequencing by the company, and identifying for the successful construction of the targeting plasmid.

The constructed CRSAPR/Cas9 vector was designated as CMAH-PX330, with a full nucleotide sequence as set forth in SEQ ID No:5.

III. β4GalNT2-CRISPR/Cas9 Vector was Constructed through the Following Method:

First, in accordance with the porcine β4GalNT2 gene sequence disclosed by Genbank, exon8 of the β4GalNT2 gene was selected as the CRISPR/Cas9 target. In accordance with the design principles of cas9 target: 5'end was G, 3'end was a PAM sequence (NGG), the guide sequence was designed as GGTAGTACTCACGAACACTC, as shown in FIG. 1, the nucleotide sequence was set forth in SEQ ID No:3.

The β4GalNT2-CRISPR/Cas9 vector was constructed through the following method:

Step (1), in accordance with the design principles of cas9 target that 5' end was G and 3' end was a PAM sequence (NGG), finding the targeting site in the β4GalNT2 gene;

Step (2), purchasing a pX330 skeleton plasmid expressing hSpCas9 and gRNA (Addgene plasmid 423230); and Step (3), synthesizing the 5' end phosphorylated oligonucleotide chain SgRNA sequence GGTAGTACT-CACGAACACTC (SEQ ID NO: 3) by the company.

The SgRNA sequence was cloned into pX330 skeleton vector in the following specific steps:

1. Digesting 1ug of pX330 plasmid with a restriction enzyme BbsI;
2. Isolating the digested pX330 plasmid by an agarose gel (an agarose gel at a concentration of 1%, i.e., 1 g of an agarose gel was added into a 100 mL electrophoresis buffer), followed by purifying and recovering the digested product with a gel extraction kit (QIAGEN);
3. Annealing the synthesized 5'end phosphorylated oligonucleotide chain SgRNA sequence in accordance with the following procedures:
   37° C. 30 min
   95° C. 5 min, and then cooling to 25° C. at a rate of 5° C./min.
4. Initiating a linking reaction in accordance with the following system: Reaction at room temperature for 10 min
   The BbsI-digested pX330 obtained in step 2 50 ng
   The annealed 5'end phosphorylated oligonucleotide obtained in step 3 (1:250 v/v, diluted with sterile water) 1 μL
   2× flashlinking buffer (NEB) 5 μL
   Diluting the system to 10 μL with ddH$_2$O
   Sub-total 10 μL
   Flash ligase (NEB) 1 μL
   Total 11 μL
5. Treating the linking system with a plasmid-safe exonuclease to remove the improperly linked plasmid:
   The linking reaction system obtained in step 4 11 μL
   10× plasmid-safe buffer (NEB) 1.5 μL
   10 mM ATP 1.5 μL
   Plasmid-safe exonuclease (NEB) 1 μL
   Total 15 ∞L
   Reaction at 37° C. for 30 min
6. Transforming
   (1) 50 μL of competent cells (TIANGEN) were placed in an ice bath;
   (2) 15 μL of a solution free of the improperly linked plasmid obtained in step 5 was added to a centrifuge tube containing the competent cells, and stood in the ice bath for 30 min after uniformly mixed;
   (3) The competent cells ice-cooled for 30 min were placed in a water bath at 42° C. for 60-90 s, and then rapidly transferred into the ice bath, allowing the cells to cool for 2-3 min;
   (4) 900 μL of a sterile LB medium (free of antibiotics) was added into the centrifuge tube, and placed on a 37° C. shaker for shaking culture at 150 rpm for 45 min after uniformly mixed; and
   (5) The centrifuge tube was placed in a centrifuge to undergo a centrifugation at 12000 rpm for 5 min, and then 900 μL of supernatant was discarded, and the precipitates of competent cells were re-suspended in the residual 100 uL of supernatant, and the re-suspended competent cells were added onto an LB solid agar medium containing the corresponding antibiotic, uniformly spread with a sterile spreading rod, and the LB solid agar medium coated with the competent cells was incubated by reversion in a 37° C. incubator for 12-16 h.
7. Carefully extracting the plasmid, sequencing by the company, and identifying for the successful construction of the targeting plasmid.

The constructed CRSAPR/Cas9 vector was designated as β4GalNT2-PX330, with a full nucleotide sequence as set forth in SEQ ID No:6.

Figure 2:
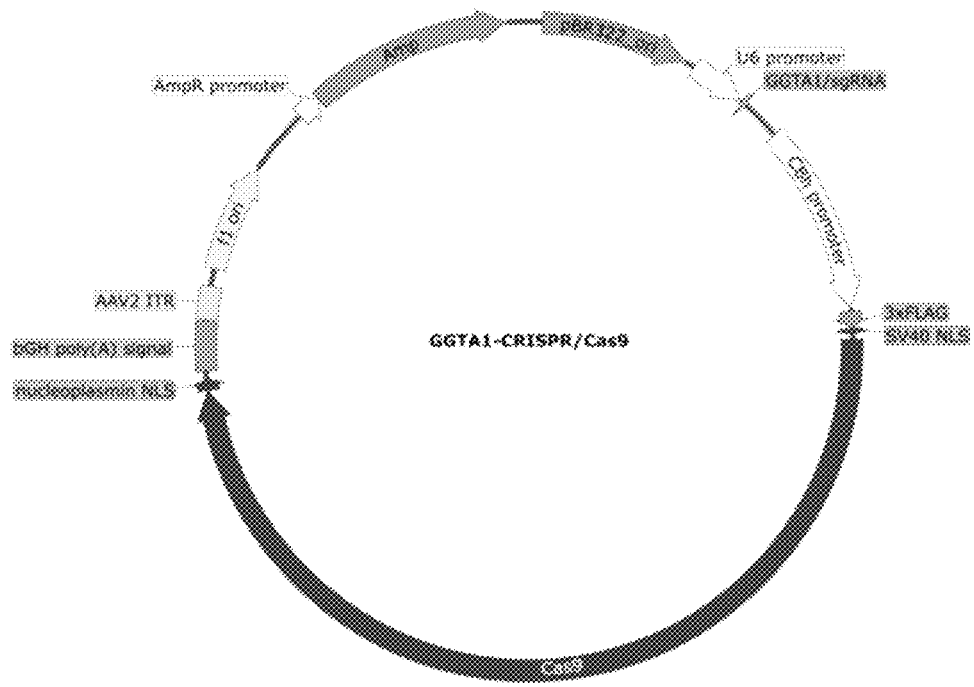
FIG. 2 is a schematic diagram of GGTA1-CRISPR/Cas9 vector.
Figure 3:
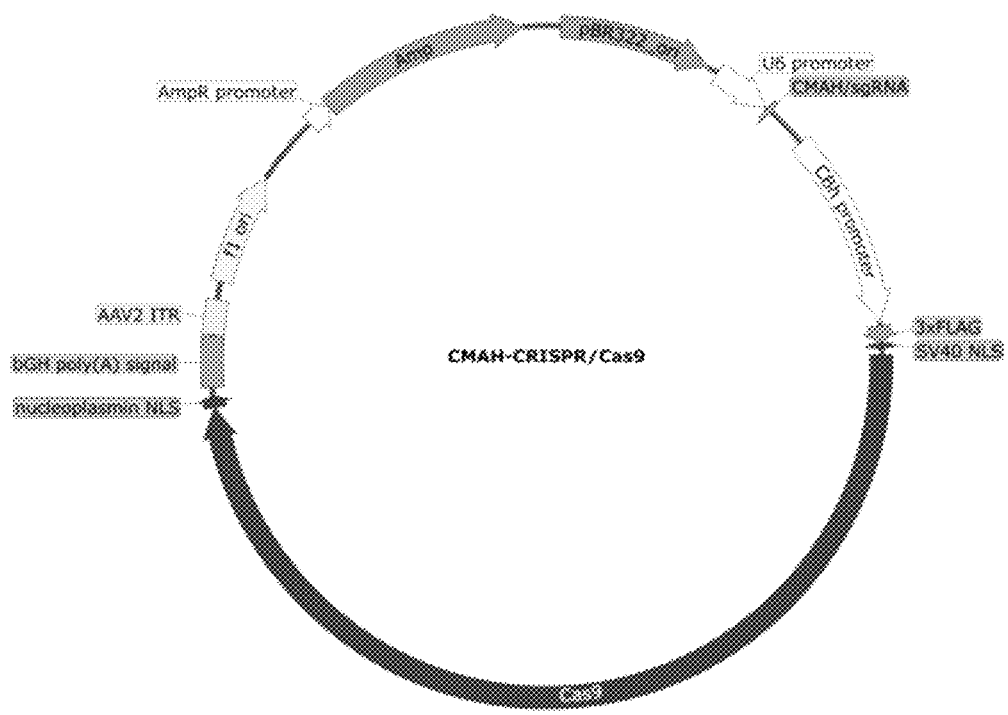
FIG. 3 is a schematic diagram of the CMAH-CRISPR/Cas9 vector.
Figure 4:
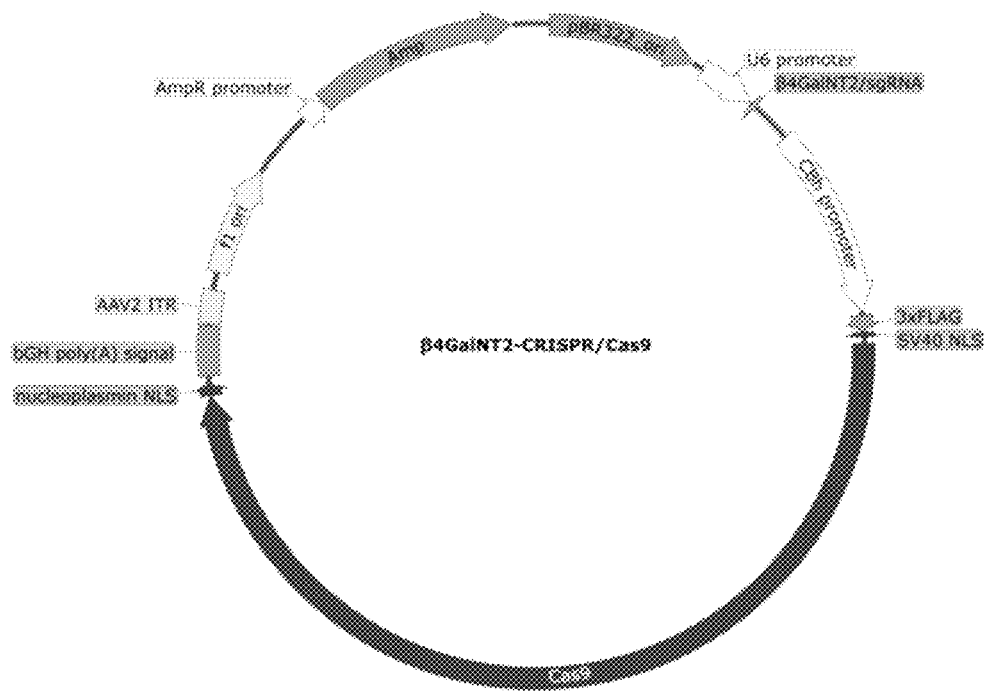
FIG. 4 is a schematic diagram of β4GalNT2-CRISPR/Cas9 vector.
Figure 5:
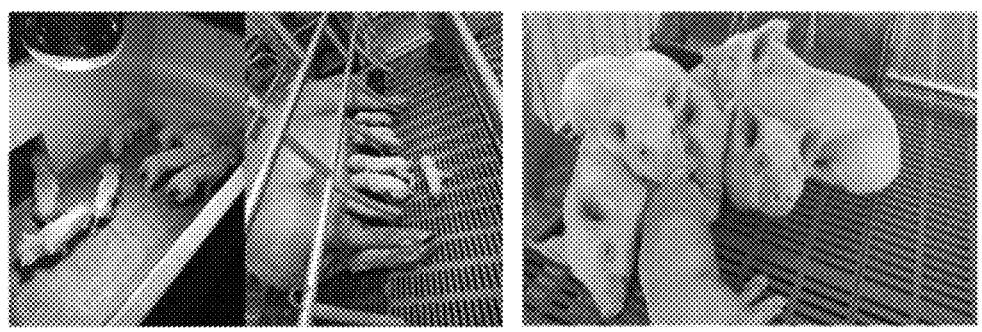
FIG. 5 shows a photograph (A) of three-knockout piglets born after somatic cell nuclear transfer at birth and after weaning and genotype identification results (B)

This transgene fragment that can be widely present in mammals and respectively express GGTA1/CMAH/β4GalNT2 genes (see FIGS. 2, 3 and 4) contains a U6 promoter, an enhancer of CMV with chicken β-actin (CMV-chicken-β-actin enhancer) gene, and has a resistant gene—neomycin (Neomycin) gene—for use in screening in mammalian cells and a resistant gene—ampicillin (ampicillin) gene—for use in screening in prokaryotic cells. This U6 promoter of a widely expressed β-skeletal muscle actin (CMV-chicken-β-actin promoter) gene can ensure the widespread expression of downstream genes.

Example 2

Construction of GGTA1/CMAH/β4GalNT2 Three-Knockout Porcine by Means of Somatic Cell Cloning The constructed GGTA1-CRISPR/Cas9 vector, CMAH-CRISPR/Cas9 vector and β4GalNT2-CRISPR/Cas9 vector, together with tdTomato plasmid were co-transfected into pig fetal fibroblasts. Single cell clones were obtained by G418 screening. GGTA1/CMAH/β4GalNT2 three-knockout pig fetal fibroblasts were obtained by sequencing identification. GGTA1/CMAH/β4GalNT2 three-knockout Landraces were prepared by somatic cell nuclear transfer (SCNT). The genome of the newly born piglet was extracted, amplified by use of a PCR primer, and linked to a T vector for genotype identification.

Step (1), porcine primary fibroblast resuscitation

1. The cryopreserved primary porcine fibroblasts were removed from liquid nitrogen, and thawed in a 37° C. water bath;
2. The thawed cells were transferred into a 15 mL sterile centrifuge tube, and then 3 mL of cell culture medium was added, the mixture was centrifuged at 1500 rpm for 5 min, wherein,
   the formula of the complete cell culture medium includes: 16% of fetal bovine serum (Gibco)+84% of DMEM medium (Gibco), in which 16% and 84% are volume percentages.
3. The supernatant was discarded. 2 mL of complete medium was added to re-suspend the cell precipitates, then, the re-suspended cells were spread into a 6-cm cell culture dish, supplemented with 2 mL of complete medium, and placed in a constant temperature incubator at 37° C., 5% $CO_2$ (volume percentage) for culture;

4. When the cells were grown to about 90% of the bottom of the dish, 0.05% (5 g/100 mL) of trypsin was used to digest the cells, and then a complete medium was added to quench the digestion. The cell suspension was transferred to a 15 mL centrifuge tube, centrifuged at 1500 rpm for 5 min, and then the supernatant was discarded, the cells were re-suspended with 2 mL of complete medium, the cells were counted, and the total amount of cells was adjusted to $1.5\times10^6$ for use in the next nuclear transfection experiment.

Step (2), Co-transfection of porcine primary fibroblasts with the constructed GGTA1-PX330, CMAH-PX330, β4GalNT2-PX330 and tdTomato plasmid (Clontech, PT4069-5)

The nucleus transfection experiment was carried out by use of Mammalian fibroblast nuclear transfection kit (Lonza) and Lonza Nucleofactor™2b Nucleus Transfector 1. A nucleus transfection reaction solution was formulated. The system was as follows:

Nucleus transfection basic solution 82 μL
Supplementary components 8 μL

2. The three constructed plasmids and the Tdtomato plasmid were added into 100 μL of nucleus transfection reaction solution obtained in step 1 at a mass ratio of 5:1, respectively, and uniformly mixed, be careful not to generate bubbles during the process;

3. The cell suspension prepared in step (1) was washed with 2× Dulbecco's Phosphate Buffered Saline (DPBS) (Gibco), and digested at 37° C. for 2 min. After terminating the digestion with DMEM complete medium containing 10 vol % of fetal bovine serum, the mixture was subject to centrifuge at 1500 rpm for 5 min. The supernatant was discarded, and the cells were re-suspended in the nucleus transfection reaction solution including plasmids obtained in this step 2. During the re-suspension processing, the generation of bubbles should be avoided.

4. The nucleus transfection system was carefully added into an electrotransfection cup provided in the kit, taking care to prevent air bubbles. The electrotransfection cup containing 100 μL of PBS was first placed in the cup slot of the Lonza nucleus transfector. The U023 nucleus transfection program was selected and debugged. Then, the electrotransfection cup containing cells was subject to electrotransfection under electroshock, immediately followed by gently sucking out the liquid in the electrotransfection cup in an ultra-clean table, which was transferred into 1 mL of DMEM complete medium containing 16% fetal bovine serum by volume, and gently mixed to uniform;

5. Several Petri dishes (10 cm) containing 8 mL of complete culture medium were prepared, and the nucleus-transfected cell suspension was pipetted into the Petri dishes containing complete medium, and mixed to uniform. The cells were observed under the microscope for their number, and counted, so that a dish included about 50-60 cells in a field of view under the microscope. Cell suspensions were added to the remaining dishes according to the final amount of this cell suspension, mixed to uniform, and placed in a constant temperature incubator at 37° C., 5% $CO_2$ for culture.

Step (3), Screening of three-knockout cell lines

1. The cells obtained in Step (2) were cultured for 24 h, and then the cell culture medium was replaced with a complete medium containing 1 mg/mL of G418, and placed in a constant temperature incubator at 37° C., 5% $CO_2$ for culture. The cell culture medium was changed every 2-3 days. During this time, the concentration of G418 was gradually decreased in accordance with the cell growth conditions until the final concentration of G418 was 0.3 mg/mL. At Days 10 to 14, monoclonal cell lines having G418 resistance would gradually grow in the culture dish;

2. A cloning ring was used to pick up the cell lines. The picked monoclonal cell lines were seeded into a 24-well plate plated with 0.3 mg/mL G418 complete medium, and placed in a constant temperature incubator at 37° C., 5% $CO_2$ for culture. The cell culture medium was changed every 2-3 days;

3. Once the cells in the 24-well plate covered the bottom of the wells, trypsin was used to digest and collect the cells, wherein ⅘ of the cells were seeded into a 12-well plate or a 6-well plate containing 0.3 mg/mL G418 complete medium (in accordance with cell numbers), and the remaining ⅕ of cells were left in the 24-well plate for further culture;

4. Once the cells in the 12-well plate or the 6-well plate covered the bottom of the wells, 0.05% (5 g/100 mL) of trypsin was used to digest and collect the cells. The cells were frozen for storage with a cell cryopreservation solution (90% fetal bovine serum+10% DMSO, volume ratio);

Step (4), Gene identification of three-knockout cell lines

1. Once the cells in the 24-well plate grew to cover the bottom of the wells, 0.05% (5 g/100 mL) of trypsin was used to digest and collect the cells. Then, 25 ml of NP-40 lysate was added to the cells to lyse the cells to extract the cell genome DNA. The lysis procedure is: 55° C. 60 min −95° C. 5 min −4° C. After the completion of the reaction, the genome DNA was stored at −20° C.;

2. The respective PCR primers were designed against the GGTA1/CMAH/β4GalNT2 gene targeting information, and the PCR primer sequences are respectively:

GGTA1

Forward primer: 5'-CCTTAGTATCCTTCCCAACCCA-GAC-3', the nucleotide sequence was as set forth in SEQ ID NO: 10, Reverse primer: 5'-GCTTTCTTTACGGTGTCAGT-GAATCC-3, the nucleotide sequence was asset forth in SEQ ID NO: 11, The PCR target product has a length of 428 bp;

CMAH

Forward primer: 5'-CTTGGAGGTGATTTGAGTTGGG-3', the nucleotide sequence was as set forth in SEQ ID NO: 12, Reverse primer: 5'-CATTTTCTTCGGAGTTGAGGGC-3', the nucleotide sequence was as set forth in SEQ ID NO: 13, The PCR target product has a length of 485 bp;

β4GalNT2

Forward primer: 5'-CCCAAGGATCCTGCTGCC-3', the nucleotide sequence was as set forth in SEQ ID NO: 14, Reverse primer: 5'-CGCCGTGTAAAGAAACCTCC-3', the nucleotide sequence was as set forth in SEQ ID NO: 15, The PCR target product has a length of 399 bp;

3. A PCR reaction was used to amplify the GGTA1/CMAH/β4GalNT2 target gene, and the PCR reaction system is as follows:

Cell genome DNA 2 μL
GGTA1 forward primer (10 pM) 1 μL
GGTA1 reverse primer (10 pM) 1 μL
2× Taq enzyme premix solution 25 μL
dd $H_2O$ 21 μL
Total 50 μL The reaction conditions are as follows:

| Step 1 | 95° C. | 5 min | |
|---|---|---|---|
| Step 2 | 95° C. | 30 s | |
| | 64° C. | 30 s | 35 cycles |
| | 72° C. | 45 s | |
| Step 3 | 72° C. | 7 min | |
| Step 4 | 4° C. | ∞ | |

The amplification of CMAH target gene is the same as the aforesaid steps; and the amplification of β4GalNT2 target gene is the same as the aforesaid steps.

10-15 monoclonal colonies were picked from the medium cultured overnight, and sequenced by the sequencing company. The sequencing results were compared with the target GGTA1/CMAH/β4GalNT2 information to determine whether the cell lines were GGTA1/CMAH/β4GalNT2 gene knockout cell lines;

A total of 27 monoclonal cell lines were picked at this time, in which one bi-allelic knockout cell line with three genes knocked out at the same time is available, and the number was 50 #. The status of this clonal genotype is shown in Table 1:

TABLE 1

Gene Identification of Landrace Fibroblasts with GGTA1/CMAH/β4GalNT2 Gene Knockout

| | | |
|---|---|---|
| GGTA | TTTTCCCAGGAGAAAATAATGAATGTCAAAGGAAGAGTGGTTCTGTCWT (the nucleotide sequence was as set forth in SEQ ID NO: 16) | |
| 50# | TTTTCCCAGGAGAAAATAATGAATGTtCAAAGGAAGAGTGGTTCTGTC (the nucleotide sequence was as set forth in SEQ ID NO: 17) | +1 |
| CMAH | AGGTCCATGCAGGCGTGAGTAAGGTACGTGATCTGTTGGAAGACAGTWT (the nucleotide sequence was as set forth in SEQ ID NO: 18) | |
| 50# | AGGTCCATGCAGGCGTGAGTAAaGGTACGTGATCTGTTGGAAGACAGT (the nucleotide sequence was as set forth in SEQ ID NO: 19) | +1 |
| β4GalNT2 | GGGTAGTACTCACGAACACTCCGGAGCATGGTCATGAGCTTGTGGGGWT (the nucleotide sequence was as set forth in SEQ ID NO: 20) | |
| 50# | GGGTAGT---------ACTCCGGAGCATGGTCATGAGCTTGTGGGG (the nucleotide sequence was as set forth in SEQ ID NO: 21) | -10 |

4. The PCR reaction product was subject to an agarose gel electrophoresis (1%, i.e., 1 g of an agarose gel was added into 100 mL of electrophoresis buffer). After the completion of electrophoresis, the target band was cut under ultraviolet light, and then recovered with a gel extraction kit (QIAGEN). The recovered PCR product was tested for concentration by NanoDrop 200;

5. The recovered PCR product was linked to a T vector by a TAKARA pMD™18-T Vector Cloning Kit, and the T vector has the following reaction system:

pMD18-T vector 1 μL gel-recovered PCR product 81.7 ng*

The system was diluted with ddH$_2$O to 10 uL

*NOTE: In the instructions of the TAKARA pMD™ 18-T Vector Cloning Kit, the dosage of Insert DNA (in this case, the gel-recovered PCR product) in the description is required to be 0.1-0.3 pM. In this case, the dosage is selected as 0.2 pM. The calculation method of dosage is: dosage of Insert DNA (ng)=number of nmol×660×the bp number of Insert DNA.

The reaction conditions of T-vector linking is reacted at 16° C. for 30 min;

6. The T vector linked product obtained in step 5 was transformed with competent cells (TIANGEN). After transformation, the competent cells were plated on an Amp-resistant LB agar solid medium, and incubated at 37° C. in a constant temperature incubator overnight;

The knockout efficiencies of GGTA1, CMAH, β4GalNT2 gene knockout are 56%, 63% and 41%, respectively.

Comparing the GGTA1/CMAH/β4GalNT2 three-knockout with GGTA1/CMAH two-knockout, the binding to human IgM, IgG is significantly reduced, therefore, the three-knockout is necessary.

Step (5), Somatic cell nuclear transplantation

1. Ovaries of sows over the age of six months were purchased from a slaughterhouse, and immature oocytes were manually extracted from the follicles. Oocytes of better quality were picked under a microscope and placed in a constant temperature incubator of 38.5° C., 5% CO$_2$ for 42-44 h, until oocytes became mature;

2. A microscopic operating system was used to enucleate the mature oocytes in step (1), and then recover the GGTA1/CMAH/β4GalNT2 knockout monoclonal cell lines obtained in step (4). The GGTA1/CMAH/β4GalNT2 knockout cells were injected as a nuclear donor into enucleated oocytes, and each enucleated oocyte was injected with one GGTA1/CMAH/β4GalNT2 knockout cell;

3. The injected cells were activated by an electrofusion technology so that the reconstructed embryos were activated after nuclear transplantation. The embryos were placed in a 38.5° C. incubator for 5 days to develop into morula; and 4. The well-developed embryos were transplanted into the womb of the surrogate sow, which was carefully cared, and detected by B-ultrasound for its pregnancy status one month after transplantation. The surrogate sow was monitored in time until delivery.

Step (6), Genotype analysis of three-knockout Ba-Ma mini pigs

1. After birth, the GGTA1/CMAH/β4GalNT2 gene knockout piglet was cut for its ear tissue, and then a blood/cell/tissue genome DNA extraction kit (TIANGEN) was used to extract the piglet genome DNA;

2. The genome DNA of the piglet obtained in step 1 was subject to a PCR reaction. The PCR reaction conditions are the same as step 4 (3). The PCR reaction product was then sequenced by the sequencing company, and the sequencing results were compared with the GGTA1/CMAH/β4GalNT2 gene target sequence.

At this time, a total of 8 male Landraces were born, numbered as 1-8. The born 8 male piglets had the same results as cell genotype.

Valve extraction process: after perfusion, the piglet was killed and the heart was removed. The envelope outside the heart was peeled off, and then washed with 1× PBS, the fat tissue outside the pericardium was gently peeled off, and then washed with 2× PBS, fixed with 0.2% of glutaraldehyde for at least 48 h for subsequent experiments.

Example 3

Phenotype Analysis of GGTA1/CMAH/β4GalNT2 Three-Knockout Porcine

1. Knockout of GGTA1, CMAH and β4GalNT2 genes in WT porcine can effectively decrease the hyperacute immune reject reaction during xenotransplantation.

Figure 6:
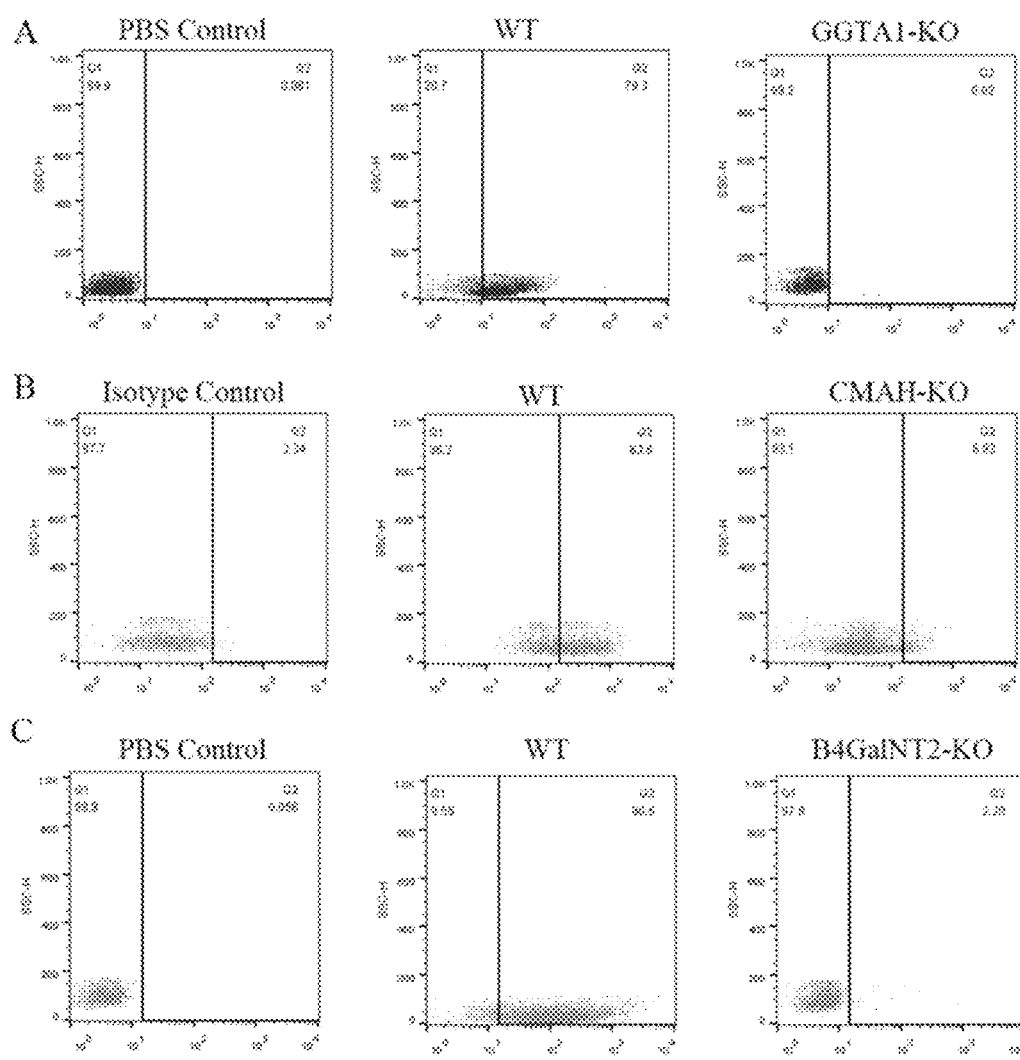
FIG. 6 shows the antigen expression in PBMC in the knockout porcine as detected by an antibody specifically binding α-1,3-galactosyltransferase (GGTA1), CMP-N-acetylneuraminic acid hydroxylase (CMAH) and β-1,4-N-acetyl galactosaminyl transferase 2 (β4GalNT2)

After weaning, the piglet was subject to blood sampling to isolate peripheral blood mononuclear cells (PBMCs). The piglet was determined by flow cytometry for its gene knockout and its binding to immunoglobulin (IgM, IgG) in human serum. It is found that the three antigens of alpha-1,3-galactosyltransferase (GGTA1), CMP-N-acetylneuraminic acid hydroxylase (CMAH) and β-1,4-N-acetyl galactosaminyl transferase 2 (β4GalNT2) were successfully knocked out in the three-knockout piglets produced by Example 2, as shown in FIG. 6, wherein PBS Control is a blank control, Isotype Control is chicken IgY, WT is a wild-type pig, GGTA1-KO is GGTA1 gene knockout pig, CMAH-KO is a CMAH gene knockout pig, and β4GalNT2-KO is a β4GalNT2 gene knockout pig. The results show that GGTA1/CMAH/β4GalNT2 knockout piglet does not express the three antigens, indicating that the three genes are successfully knocked out.

PBMC is separated by the following method: To 100 μL of anticoagulated blood was added 3 volumes of red blood cell lysate (BD, diluted with 10× deionized water). It was lysed at room temperature for 5 min-10 min. After centrifugation, the supernatant was discarded, and washed with a pre-cold washing solution containing 0.1% FBS (the solvent is PBS, 0.1%, i.e., 0.1 g FBS/100 mL PBS) (enhancing cell sedimentation), rinsed, and centrifuged to obtain PBMC precipitate.

2. Peripheral blood mononuclear cells (PBMCs) were detected by a flow cytometry for the binding level of PBMCs of three-knockout piglets and control wild-type piglets with human immunoglobin. The results show that in comparison with wild-type piglets, the three-knockout porcine exhibits a significant decrease in the binding level of PBMCs to human immunoglobulin, which is close to the level of humans.

After a commercially available human serum was inactivated in a water bath at 56° C. for 30 min, the obtained PBMC was incubated on ice for 2 h, centrifuged at 5000 rpm for 5 min, washed with 3× PBS, and blocked with goat serum at a volume ratio of 10% at 4° C. After 30 min, it was washed with 3× PBS. After human-specific immunoglobulin antibodies were incubated, it was washed with PBS to remove antibody, re-suspended, and tested for the average fluorescence intensity on the computer. The results showed that as compared to PBMC of wild-type pigs, the three-knockout pig exhibits a significant decrease in the binding level of PBMC to human immunoglobulin, which was close to that of humans under normal circumstances. As shown in FIG. 6, the GGTA1/CMAH/β4GalNT2 three-knockout pig has a significant effect on overcoming hyperacute immune reject reaction.

Figure 7:
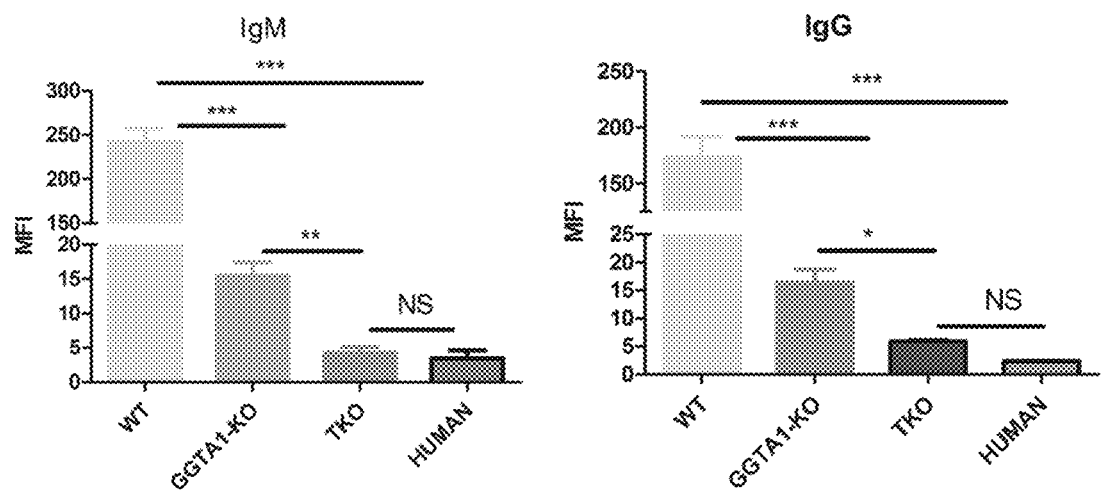
FIG. 7 shows the binding of PBMCs isolated respectively from GGTA1/CMAH/β4GalNT2 three-knockout pigs (TKO), wild-type pigs (WT), GGTA1 knockout pigs (GGTA1-KO) and human with human immunoglobin, incubated with human serum for 2 hrs, and bound to anti-IgG and anti-IgM antibodies, as detected by flow cytometry.
Figure 8:
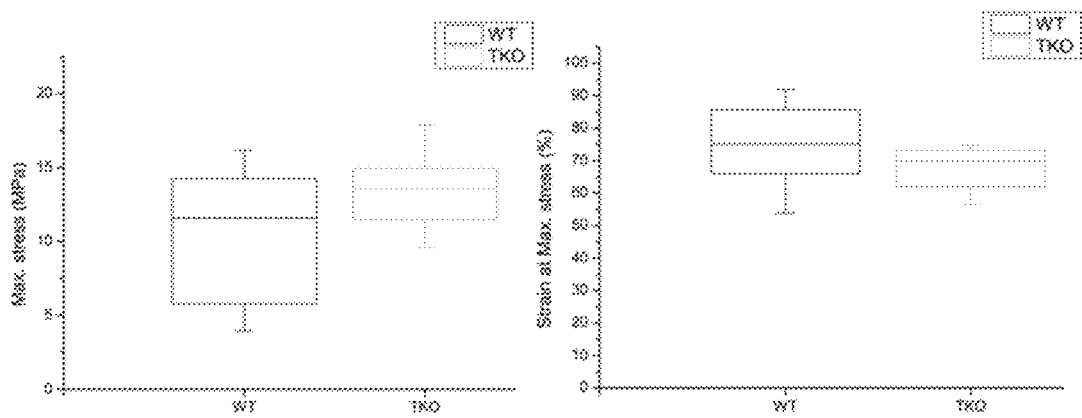
FIG. 8 is the stress-strain diagram of the GGTA1/CMAH/β4GalNT2 three-knockout pigs (TKO) and wild-type pigs (WT), wherein the left panel is the stress diagram of the heart valves of TKO and WT pigs, showing no significant difference therebetween; and the right panel is the strain of the heart valves of the TKO and WT pigs in response to the stress, and the results show that there is no significant difference therebetween.

3. Uniaxial mechanical testing of the pericardium mechanical properties of wild-type and three-knockout pigs The fresh pericardium of wild-type and three-knockout pigs was fixed with glutaraldehyde for more than 48 h. The pericardium was cut into a dumbbell shape with a length of 14 mm, a width of 2 mm, and a thickness of 2 mm. Each group included 6 samples, with a length of 14.67±1.03 mm, a width of 2.15±0.23 mm, and a thickness of 0.2±0.01 mm. An instron 5943 single column material tensile tester was used to detect the stress and strain of the pericardium. The results showed that the pericardium of three-knockout pig does not exhibit a significant difference of mechanical properties from that of the wild type, as shown in FIG. 7 and FIG. 8.

At present, the clinically used and commercially available glutaraldehyde fixed heart valve has been maturely applied in clinic, but the effect of the heart valve cannot be maintained for a long time due to calcification, immune reject reaction and the like. The heart valves of pigs in which three genes associated with immune reject reaction are knocked out can be used as a source of a new type of biomaterial valve to provide solutions to the problems that arise in clinical cardiac replacement therapy.

What is claimed is:

1. A single guide RNA (SgRNA) combination, comprising an SgRNA specifically targeting a α-1,3-galactosyltransferase (GGTA1) gene, an SgRNA specifically targeting a cytidine monophosphate-N-acetylneuraminic acid hydroxylase (CMAH) gene and an SgRNA specifically targeting a β1,4-N-acetyl galactosaminyl transferase 2 (β4GalNT2) gene; wherein, the SgRNA specifically targeting the GGTA1 gene comprises the nucleotide sequence as set forth in SEQ ID No:1, the SgRNA specifically targeting the CMAH gene comprises the nucleotide sequence as set forth in SEQ ID No:2, and the SgRNA specifically targeting the β4GalNT2 gene comprises the nucleotide sequence as set forth in SEQ ID No:3.

2. A vector combination comprising a GGTA1 vector, a CMAH vector and a β4GalNT2 vector; wherein the GGTA1 vector comprises a SgRNA specifically targeting a GGTA1 gene, and the SgRNA comprises the nucleotide sequence as set forth in SEQ ID No:1;
the CMAH vector comprises a comprises a SgRNA specifically targeting a CMAH gene, and the SgRNA comprises the nucleotide sequence as set forth in SEQ ID No:2, and
the β4GalNT2 vector comprises a SgRNA specifically targeting a β4GalNT2 gene, and the SgRNA comprises the nucleotide sequence as set forth in SEQ ID No:3.

3. The vector combination of claim 2, wherein the nucleotide sequence of said GGTA1 vector is as set forth in SEQ ID No:4; the nucleotide sequence of said CMAH vector is as set forth in SEQ ID No:5; and the nucleotide sequence of said β4GalNT2 vector is as set forth in SEQ ID No:6.

4. The vector combination of claim 2, wherein said vector is constructed through the following method:

(1) digesting a pX330 plasmid with a restriction enzyme, isolating the digested plasmid with an agarose gel, followed by purifying and recovering the digested product with a gel extraction kit;

(2) annealing the SgRNA sequence in accordance with the following procedures:
37° C. for 30 minutes,
95° C. for 5 minutes, and then cooling to 25° C. at a rate of 5° C./minute;

(3) linking the digested product obtained in step (1) to the SgRNA sequence annealed in step (2) with a ligase to form a plasmid system;

(4) treating the system obtained in step (3) with a plasmid-safe exonuclease to remove any improperly linked plasmids;

(5) transforming the plasmid into a competent cell for culture; and (6) extracting the plasmid from the competent cell cultured in step (5) for sequencing, thereby determining successful construction of the vector; wherein:

when the vector is the GGTA1 vector, the SgRNA sequence in step (2) is the nucleotide sequence set forth in SEQ ID No:1;

when the vector is the CMAH vector, the SgRNA sequence in step (2) is the nucleotide sequence set forth in SEQ ID No:2; and when the vector is the β4GalNT2 vector, the SgRNA sequence in step (2) is the nucleotide sequence set forth in SEQ ID No: 3.

5. A method of obtaining a fibroblast with the GGTA1 gene, the CMAH gene and the β4GalNT2 genes knocked out, comprising the following steps:

(1) transforming the vector combination of claim 2 into a porcine fetal fibroblast, and (2) performing a resistance screening on the fibroblast obtained in step (1) with G418 antibiotics to obtain a fibroblast having G418 resistance, and (3) subjecting the fibroblast having G418 resistance to PCR amplification gene sequencing, thereby obtaining the fibroblast with the GGTA 1 gene, the CMAH gene and the β4GalNT2 genes knocked out.

6. A method of preparing a heart valve of a pig, comprising the following steps:

(1) obtaining a pig with a GGTA1 gene, the CMAH gene and the β4GalNT2 gene knockout using the vector combination of claim 2, and (2) obtaining the heart valve from the pig of step (1).

7. The method of claim 6, wherein obtaining a pig with the GGTA1, CMAH, and β4GalNT2 genes knocked out comprises:

(a) transforming the vector combination into a porcine fetal fibroblast;

(b) performing a resistance screening on the fibroblast obtained in step (a) with G418 antibiotics to obtain a fibroblast having G418 resistance, and (c) subjecting the fibroblast having G418 resistance to PCR amplification gene sequencing, thereby obtaining the fibroblast with the GGTA1 gene, the CMAH gene and the β4GalNT2 genes knocked out;

(d) transplanting the nucleus of the fibroblast having G418 resistance into an enucleated porcine oocyte and culturing to blastocyst stage;

(e) transplanting the blastocyst obtained in step (d) into a surrogate porcine for feeding and parturition thereby yielding offspring; and (f) extracting a genome of the porcine offspring obtained in step (e), followed by amplification with a PCR primer for genotype identification.

8. A kit for knocking out the GGTA1 gene, the CMAH gene and the β4GalNT2 gene, comprising the SgRNA combination of claim 1.

* * * * *

SEQUENCE LISTING

```
<160> NUMBER OF SEQ ID NOS: 21

<210> SEQ ID NO 1
<211> LENGTH: 18
<212> TYPE: DNA
<213> ORGANISM: Artificial Sequence
<220> FEATURE:
<223> OTHER INFORMATION: GGTA1-SgRNA

<400> SEQUENCE: 1
gaaaataatg aatgtcaa                                                 18
```

```
<210> SEQ ID NO 2
<211> LENGTH: 20
<212> TYPE: DNA
<213> ORGANISM: Artificial Sequence
<220> FEATURE:
<223> OTHER INFORMATION: CMAH-SgRNA

<400> SEQUENCE: 2
gagtaaggta cgtgatctgt                                                    20

<210> SEQ ID NO 3
<211> LENGTH: 20
<212> TYPE: DNA
<213> ORGANISM: Artificial Sequence
<220> FEATURE:
<223> OTHER INFORMATION: Beta4GalNT2-SgRNA

<400> SEQUENCE: 3
ggtagtactc acgaacactc                                                    20

<210> SEQ ID NO 4
<211> LENGTH: 8505
<212> TYPE: DNA
<213> ORGANISM: Artificial Sequence
<220> FEATURE:
<223> OTHER INFORMATION: GGTA1-CRISPR/Cas9

<400> SEQUENCE: 4
tgaccaaaat cccttaacgt gagttttcgt tccactgagc gtcagacccc gtagaaaaga      60
tcaaaggatc ttcttgagat cctttttttc tgcgcgtaat ctgctgcttg caaacaaaaa     120
aaccaccgct accagcggtg gtttgtttgc cggatcaaga gctaccaact cttttttccga    180 aggtaactgg cttcagcaga gcgcagatac caaatactgt ccttctagtg tagccgtagt     240
taggccacca cttcaagaac tctgtagcac cgcctacata cctcgctctg ctaatcctgt     300
taccagtggc tgctgccagt ggcgataagt cgtgtcttac cgggttggac tcaagacgat     360
agttaccgga taaggcgcag cggtcgggct gaacggggg ttcgtgcaca cagcccagct     420
tggagcgaac gacctacacc gaactgagat acctacagcg tgagctatga aaagcgcca     480 cgcttcccga agggagaaag gcggacaggt atccggtaag cggcagggtc ggaacaggag     540
agcgcacgag ggagcttcca gggggaaacg cctggtatct ttatagtcct gtcgggtttc     600
gccacctctg acttgagcgt cgatttttgt gatgctcgtc aggggggcgg agcctatgga     660
aaaacgccag caacgcggcc ttttacggt tcctggcctt ttgctggcct tttgctcaca      720
tgtgagggcc tatttcccat gattccttca tatttgcata tacgatacaa ggctgttaga     780
gagataattg gaattaattt gactgtaaac acaaagatat tagtacaaaa tacgtgacgt     840
agaaagtaat aatttcttgg gtagtttgca gttttaaaat tatgttttaa aatggactat     900
catatgctta ccgtaacttg aaagtatttc gatttcttgg ctttatatat cttgtggaaa     960
ggacgaaaca ccgaaaataa tgaatgtcaa gttttagagc tagaaatagc aagttaaaat    1020
aaggctagtc cgttatcaac ttgaaaaagt ggcaccgagt cggtgctttt tgttttaga    1080 gctagaaata gcaagttaaa ataaggctag tccgttttta gcgcgtgcgc caattctgca    1140
gacaaatggc tctagaggta cccgttacat aacttacggt aaatggcccg cctggctgac    1200
cgcccaacga cccccgccca ttgacgtcaa tagtaacgcc aatagggact tccattgac    1260 gtcaatgggt ggagtattta cggtaaactg cccacttggc agtacatcaa gtgtatcata    1320
tgccaagtac gccccctatt gacgtcaatg acggtaaatg gcccgcctgg cattgtgccc    1380
```

```
agtacatgac cttatgggac tttcctactt ggcagtacat ctacgtatta gtcatcgcta    1440
ttaccatggt cgaggtgagc cccacgttct gcttcactct ccccatctcc ccccctccc     1500 caccccaat tttgtattta tttatttttt aattattttg tgcagcgatg ggggcggggg     1560
gggggggggg gcgcgcgcca ggcggggcgg ggcggggcga ggggcggggc ggggcgaggc    1620
ggagaggtgc ggcggcagcc aatcagagcg gcgcgctccg aaagtttcct tttatggcga    1680
ggcggcggcg gcgcggcccc tataaaaagc gaagcgcgcg gcgggcggga gtcgctgcga    1740
cgctgccttc gccccgtgcc ccgctccgcc gccgcctcgc gccgcccgcc ccggctctga    1800
ctgaccgcgt tactcccaca ggtgagcggg cgggacggcc cttctcctcc gggctgtaat    1860
tagctgagca agaggtaagg gtttaaggga tggttggttg gtggggtatt aatgtttaat    1920
tacctggagc acctgcctga aatcactttt tttcaggttg gaccggtgcc accatggact    1980
ataaggacca cgacggagac tacaaggatc atgatattga ttacaaagac gatgacgata    2040
agatggcccc aaagaagaag cggaaggtcg gtatccacgg agtcccagca gccgacaaga    2100
agtacagcat cggcctggac atcggcacca actctgtggg ctgggccgtg atcaccgacg    2160
agtacaaggt gcccagcaag aaattcaagg tgctgggcaa caccgaccgg cacagcatca    2220
agaagaacct gatcggagcc ctgctgttcg acagcggcga aacagccgag gccacccggc    2280
tgaagagaac cgccagaaga agatacacca gacggaagaa ccggatctgc tatctgcaag    2340
agatcttcag caacgagatg gccaaggtgg acgacagctt cttccacaga ctggaagagt    2400
ccttcctggt ggaagaggat aagaagcacg agcggcaccc catcttcggc aacatcgtgg    2460
acgaggtggc ctaccacgag aagtacccca ccatctacca cctgagaaag aaactggtgg    2520
acagcaccga caaggccgac ctgcggctga tctatctggc cctggcccac atgatcaagt    2580
tccggggcca cttcctgatc gagggcgacc tgaaccccga caacagcgac gtggacaagc    2640
tgttcatcca gctggtgcag acctacaacc agctgttcga ggaaaacccc atcaacgcca    2700
gcggcgtgga cgccaaggcc atcctgtctg ccagactgag caagagcaga cggctggaaa    2760
atctgatcgc ccagctgccc ggcgagaaga gaatggcct gttcggaaac ctgattgccc    2820
tgagcctggg cctgaccccc aacttcaaga gcaacttcga cctggccgag gatgccaaac    2880
tgcagctgag caaggacacc tacgacgacg acctggacaa cctgctggcc cagatcggcg    2940
accagtacgc cgacctgttt ctggccgcca agaacctgtc cgacgccatc ctgctgagcg    3000
acatcctgag agtgaacacc gagatcacca aggccccccct gagcgcctct atgatcaaga    3060
gatacgacga gcaccaccag gacctgaccc tgctgaaagc tctcgtgcgg cagcagctgc    3120
ctgagaagta caaagagatt ttcttcgacc agagcaagaa cggctacgcc ggctacattg    3180
acggcggagc cagccaggaa gagttctaca agttcatcaa gcccatcctg gaaaagatgg    3240
acggcaccga ggaactgctc gtgaagctga acagagagga cctgctgcgg aagcagcgga    3300
ccttcgacaa cggcagcatc ccccaccaga tccacctggg agagctgcac gccattctgc    3360
ggcggcagga agattttttac ccattcctga aggacaaccg ggaaaagatc gagaagatcc    3420
tgaccttccg catcccctac tacgtgggcc ctctggccag gggaaacagc agattcgcct    3480
ggatgaccag aaagagcgag gaaaccatca cccccctggaa cttcgaggaa gtggtggaca    3540
agggcgcttc cgcccagagc ttcatcgagc ggatgaccaa cttcgataag aacctgccca    3600
acgagaaggt gctgcccaag cacagcctgc tgtacgagta cttcaccgtg tataacgagc    3660
tgaccaaagt gaaatacgtg accgagggaa tgagaaagcc cgccttcctg agcggcgagc    3720
```

```
agaaaaaggc catcgtggac ctgctgttca agaccaaccg gaaagtgacc gtgaagcagc    3780
tgaaagagga ctacttcaag aaaatcgagt gcttcgactc cgtggaaatc tccggcgtgg    3840
aagatcggtt caacgcctcc ctgggcacat accacgatct gctgaaaatt atcaaggaca    3900
aggacttcct ggacaatgag gaaaacgagg acattctgga agatatcgtg ctgaccctga    3960
cactgtttga ggacagagag atgatcgagg aacggctgaa aacctatgcc cacctgttcg    4020
acgacaaagt gatgaagcag ctgaagcggc ggagatacac cggctggggc aggctgagcc    4080
ggaagctgat caacggcatc cgggacaagc agtccggcaa gacaatcctg gatttcctga    4140
agtccgacgg cttcgccaac agaaacttca tgcagctgat ccacgacgac agcctgacct    4200
ttaaagagga catccagaaa gcccaggtgt ccggccaggg cgatagcctg cacgagcaca    4260
ttgccaatct ggccggcagc cccgccatta gaaagggcat cctgcagaca gtgaaggtgg    4320
tggacgagct cgtgaaagtg atgggccggc acaagcccga gaacatcgtg atcgaaatgg    4380
ccagagagaa ccagaccacc cagaagggac agaagaacag ccgcgagaga atgaagcgga    4440
tcgaagaggg catcaaagag ctgggcagcc agatcctgaa agaacacccc gtggaaaaca    4500
cccagctgca gaacgagaag ctgtacctgt actacctgca gaatgggcgg gatatgtacg    4560
tggaccagga actggacatc aaccggctgt ccgactacga tgtggaccat atcgtgcctc    4620
agagctttct gaaggacgac tccatcgaca caaggtgct gaccagaagc gacaagaacc    4680
ggggcaagag cgacaacgtg ccctccgaag aggtcgtgaa aaagatgaag aactactggc    4740
ggcagctgct gaacgccaag ctgattaccc agagaaagtt cgacaatctg accaaggccg    4800
agagaggcgg cctgagcgaa ctggataagg ccggcttcat caagagacag ctggtggaaa    4860
cccggcagat cacaaagcac gtggcacaga tcctggactc ccggatgaac actaagtacg    4920
acgagaatga caagctgatc cgggaagtga aagtgatcac cctgaagtcc aagctggtgt    4980
ccgatttccg gaaggatttc cagttttaca aagtgcgcga gatcaacaac taccaccacg    5040
cccacgacgc ctacctgaac gccgtcgtgg gaaccgccct gatcaaaaag taccctaagc    5100
tggaaagcga gttcgtgtac ggcgactaca aggtgtacga cgtgcggaag atgatcgcca    5160
agagcgagca ggaaatcggc aaggctaccg ccaagtactt cttctacagc aacatcatga    5220
acttttttca gaccgagatt accctggcca acggcgagat ccggaagcgg cctctgatcg    5280
agacaaacgg cgaaaccggg gagatcgtgt gggataaggg ccgggatttt gccaccgtgc    5340
ggaaagtgct gagcatgccc caagtgaata tcgtgaaaaa gaccgaggtg cagacaggcg    5400
gcttcagcaa agagtctatc ctgcccaaga ggaacagcga taagctgatc gccagaagaa    5460
aggactggga ccctaagaag tacggcggct tcgacagccc caccgtggcc tattctgtgc    5520
tggtggtggc caaagtggaa aagggcaagt ccaagaaact gaagagtgtg aaagagctgc    5580
tggggatcac catcatggaa agaagcagct tcgagaagaa tcccatcgac tttctggaag    5640
ccaagggcta caaagaagtg aaaaaggacc tgatcatcaa gctgcctaag tactccctgt    5700
tcgagctgga aaacggccgg aagagaatgc tggcctctgc cggcgaactg cagaagggaa    5760
acgaactggc cctgccctcc aaatatgtga acttcctgta cctggccagc cactatgaga    5820
agctgaaggg ctccccgag gataatgagc agaaacagct gtttgtggaa cagcacaagc    5880
actacctgga cgagatcatc gagcagatca gcgagttctc caagagagtg atcctggccg    5940
acgctaatct ggacaaagtg ctgtccgcct acaacaagca ccgggataag cccatcagag    6000
agcaggccga gatatcatc cacctgtttt ccctgaccaa tctgggagcc cctgccgcct    6060
tcaagtactt tgacaccacc atcgaccgga agaggtacac cagcaccaaa gaggtgctgg    6120
```

```
acgccaccct gatccaccag agcatcaccg gcctgtacga gacacggatc gacctgtctc    6180
agctgggagg cgacaaaagg ccggcggcca cgaaaaaggc cggccaggca aaaagaaaa     6240 agtaagaatt cctagagctc gctgatcagc ctcgactgtg ccttctagtt gccagccatc    6300
tgttgtttgc ccctcccccg tgccttcctt gaccctggaa ggtgccactc ccactgtcct    6360
ttcctaataa aatgaggaaa ttgcatcgca ttgtctgagt aggtgtcatt ctattctggg    6420
gggtggggtg gggcaggaca gcaaggggga ggattgggaa gagaatagca ggcatgctgg    6480
ggagcggccg caggaacccc tagtgatgga gttggccact ccctctctgc gcgctcgctc    6540
gctcactgag gccgggcgac caaaggtcgc ccgacgcccg ggctttgccc gggcggcctc    6600
agtgagcgag cgagcgcgca gctgcctgca ggggcgcctg atgcggtatt ttctccttac    6660
gcatctgtgc ggtatttcac accgcatacg tcaaagcaac catagtacgc gccctgtagc    6720
ggcgcattaa gcgcggcggg tgtggtggtt acgcgcagcg tgaccgctac acttgccagc    6780
gccctagcgc ccgctccttt cgctttcttc ccttcctttc tcgccacgtt cgccggcttt    6840
ccccgtcaag ctctaaatcg ggggctccct ttagggttcc gatttagtgc tttacggcac    6900
ctcgacccca aaaaacttga tttgggtgat ggttcacgta gtgggccatc gccctgatag    6960 acggttttc  gccctttgac gttggagtcc acgttcttta atagtggact cttgttccaa    7020
actggaacaa cactcaaccc tatctcgggc tattctttg  atttataagg gattttgccg    7080
atttcggcct attggttaaa aaatgagctg atttaacaaa aatttaacgc gaattttaac    7140
aaaatattaa cgtttacaat tttatggtgc actctcagta caatctgctc tgatgccgca    7200
tagttaagcc agccccgaca cccgccaaca cccgctgacg cgccctgacg ggcttgtctg    7260
ctcccggcat ccgcttacag acaagctgtg accgtctccg ggagctgcat gtgtcagagg    7320
ttttcaccgt catcaccgaa acgcgcgaga cgaaagggcc tcgtgatacg cctattttta    7380
taggttaatg tcatgataat aatggtttct tagacgtcag gtggcacttt tcggggaaat    7440
gtgcgcggaa cccctatttg tttatttttc taaatacatt caaatatgta tccgctcatg    7500
agacaataac cctgataaat gcttcaataa tattgaaaaa ggaagagtat gagtattcaa    7560
catttccgtg tcgcccttat tcccttttt  gcggcatttt gccttcctgt ttttgctcac    7620
ccagaaacgc tggtgaaagt aaaagatgct gaagatcagt tgggtgcacg agtgggttac    7680
atcgaactgg atctcaacag cggtaagatc cttgagagtt ttcgccccga agaacgtttt    7740
ccaatgatga gcacttttaa agttctgcta tgtggcgcgg tattatcccg tattgacgcc    7800
gggcaagagc aactcggtcg ccgcatacac tattctcaga atgacttggt tgagtactca    7860
ccagtcacag aaaagcatct tacggatggc atgacagtaa gagaattatg cagtgctgcc    7920
ataaccatga gtgataacac tgcggccaac ttacttctga caacgatcgg aggaccgaag    7980
gagctaaccg cttttttgca acatggggg  atcatgtaa  ctcgccttga tcgttgggaa    8040
ccggagctga atgaagccat accaaacgac gagcgtgaca ccacgatgcc tgtagcaatg    8100
gcaacaacgt tgcgcaaact attaactggc gaactactta ctctagcttc ccggcaacaa    8160
ttaatagact ggatggaggc ggataaagtt gcaggaccac ttctgcgctc ggcccttccg    8220
gctggctggt ttattgctga taaatctgga gccggtgagc gtggaagccg cggtatcatt    8280
gcagcactgg ggccagatgg taagccctcc cgtatcgtag ttatctacac gacggggagt    8340
caggcaacta tggatgaacg aaatagacag atcgctgaga taggtgcctc actgattaag    8400
cattggtaac tgtcagacca agtttactca tatatacttt agattgattt aaaacttcat    8460
```

```
                                              -continued
tttttaattta aaaggatcta ggtgaagatc cttttttgata atctc              8505

<210> SEQ ID NO 5
<211> LENGTH: 8508
<212> TYPE: DNA
<213> ORGANISM: Artificial Sequence
<220> FEATURE:
<223> OTHER INFORMATION: CMAH-CRISPR/Cas9

<400> SEQUENCE: 5
atgaccaaaa tcccttaacg tgagttttcg ttccactgag cgtcagaccc cgtagaaaag   60
atcaaaggat cttcttgaga tcctttttt ctgcgcgtaa tctgctgctt gcaaacaaaa  120
aaaccaccgc taccagcggt ggtttgtttg ccggatcaag agctaccaac tcttttttccg  180 aaggtaactg gcttcagcag agcgcagata ccaaatactg tccttctagt gtagccgtag  240
ttaggccacc acttcaagaa ctctgtagca ccgcctacat acctcgctct gctaatcctg  300
ttaccagtgg ctgctgccag tggcgataag tcgtgtctta ccgggttgga ctcaagacga  360
tagttaccgg ataaggcgca gcggtcgggc tgaacggggg gttcgtgcac acagcccagc  420
ttggagcgaa cgacctacac cgaactgaga tacctacagc gtgagctatg agaaagcgcc  480
acgcttcccg aagggagaaa ggcggacagg tatccggtaa gcggcagggt cggaacagga  540
gagcgcacga gggagcttcc agggggaaac gcctggtatc tttatagtcc tgtcgggttt  600
cgccacctct gacttgagcg tcgatttttg tgatgctcgt caggggggcg agcctatgg   660 aaaaacgcca gcaacgcggc cttttacgg ttcctggcct tttgctggcc ttttgctcac   720
atgtgagggc ctatttccca tgattccttc atatttgcat atacgataca aggctgttag   780
agagataatt ggaattaatt tgactgtaaa cacaaagata ttagtacaaa atacgtgacg   840
tagaaagtaa taatttcttg ggtagtttgc agttttaaaa ttatgtttta aaatggacta   900
tcatatgctt accgtaactt gaaagtattt cgatttcttg ctttatata tcttgtggaa   960 aggacgaaac accgagtaag gtacgtgatc tgtgttttag agctagaaat agcaagttaa  1020
aataaggcta gtccgttatc aacttgaaaa agtggcaccg agtcggtgct ttttttgtttt  1080 agagctagaa atagcaagtt aaaataaggc tagtccgttt ttagcgcgtg cgccaattct  1140
gcagacaaat ggctctagag gtacccgtta cataacttac ggtaaatggc ccgcctggct  1200
gaccgcccaa cgacccccgc ccattgacgt caatagtaac gccaataggg acttccatt   1260 gacgtcaatg ggtggagtat ttacggtaaa ctgcccactt ggcagtacat caagtgtatc  1320
atatgccaag tacgccccct attgacgtca atgacggtaa atggcccgcc tggcattgtg  1380
cccagtacat gaccttatgg actttccta cttggcagta catctacgta ttagtcatcg  1440
ctattaccat ggtcgaggtg agccccacgt tctgcttcac tctccccatc tcccccccct  1500 ccccacccc aattttgtat ttatttattt tttaattatt ttgtgcagcg atggggggcgg  1560 ggggggggg gggcgcgcg ccaggcgggg cggggcgggg cgaggggcgg ggcggggcga  1620
ggcggagagg tgcggcggca gccaatcaga gcggcgcgct ccgaaagttt ccttttatgg  1680
cgaggcggcg gcggcggcgg ccctataaaa agcgaagcgc gcggcgggcg ggagtcgctg  1740
cgacgctgcc ttcgccccgt gccccgctcc gccgccgcct cgcgccgccc gccccggctc  1800
tgactgaccg cgttactccc acaggtgagc gggcgggacg gcccttctcc tccgggctgt  1860
aattagctga gcaagaggta agggtttaag ggatggttgg ttggtggggt attaatgttt  1920
aattacctga gcacctgcc tgaaatcact ttttttcagg ttggaccggt gccaccatgg  1980
actataagga ccacgacgga gactacaagg atcatgatat tgattacaaa gacgatgacg  2040
```

```
ataagatggc cccaaagaag aagcggaagg tcggtatcca cggagtccca gcagccgaca    2100
agaagtacag catcggcctg acatcggca ccaactctgt gggctgggcc gtgatcaccg     2160
acgagtacaa ggtgcccagc aagaaattca aggtgctggg caacaccgac cggcacagca    2220
tcaagaagaa cctgatcgga gccctgctgt tcgacagcgg cgaaacagcc gaggccaccc    2280
ggctgaagag aaccgccaga agaagataca ccagacggaa gaaccggatc tgctatctgc    2340
aagagatctt cagcaacgag atggccaagg tggacgacag cttcttccac agactggaag    2400
agtccttcct ggtggaagag gataagaagc acgagcggca ccccatcttc ggcaacatcg    2460
tggacgaggt ggcctaccac gagaagtacc ccaccatcta ccacctgaga aagaaactgg    2520
tggacagcac cgacaaggcc gacctgcggc tgatctatct ggccctggcc cacatgatca    2580
agttccgggg ccacttcctg atcgagggcg acctgaaccc cgacaacagc gacgtggaca    2640
agctgttcat ccagctggtg cagacctaca accagctgtt cgaggaaaac cccatcaacg    2700
ccagcggcgt ggacgccaag gccatcctgt ctgccagact gagcaagagc agacggctgg    2760
aaaatctgat cgcccagctg cccggcgaga agaagaatgg cctgttcgga aacctgattg    2820
ccctgagcct gggcctgacc cccaacttca gagcaacctt cgacctggcc gaggatgcca    2880
aactgcagct gagcaaggac acctacgacg acgacctgga caacctgctg gcccagatcg    2940
gcgaccagta cgccgacctg tttctggccg ccaagaacct gtccgacgcc atcctgctga    3000
gcgacatcct gagagtgaac accgagatca ccaaggcccc cctgagcgcc tctatgatca    3060
agagatacga cgagcaccac caggacctga ccctgctgaa agctctcgtg cggcagcagc    3120
tgcctgagaa gtacaaagag attttcttcg accagagcaa gaacggctac gccggctaca    3180
ttgacggcgg agccagccag gaagagttct acaagttcat caagcccatc ctggaaaaga    3240
tggacggcac cgaggaactg ctcgtgaagc tgaacagaga ggacctgctg cggaagcagc    3300
ggaccttcga caacggcagc atcccccacc agatccacct gggagagctg cacgccattc    3360
tgcggcggca ggaagatttt tacccattcc tgaaggacaa ccgggaaaag atcgagaaga    3420
tcctgacctt ccgcatcccc tactacgtgg gccctctggc caggggaaac agcagattcg    3480
cctggatgac cagaaagagc gaggaaacca tcacccctg gaacttcgag gaagtggtgg     3540
acaagggcgc ttccgcccag agcttcatcg agcggatgac caacttcgat aagaacctgc    3600
ccaacgagaa ggtgctgccc aagcacagcc tgctgtacga gtacttcacc gtgtataacg    3660
agctgaccaa agtgaaatac gtgaccgagg gaatgagaaa gcccgccttc ctgagcggcg    3720
agcagaaaaa ggccatcgtg gacctgctgt tcaagaccaa ccggaaagtg accgtgaagc    3780
agctgaaaga ggactacttc aagaaaatcg agtgcttcga ctccgtggaa atctccggcg    3840
tggaagatcg gttcaacgcc tccctgggca cataccacga tctgctgaaa attatcaagg    3900
acaaggactt cctggacaat gaggaaaacg aggacattct ggaagatatc gtgctgaccc    3960
tgacactgtt tgaggacaga gagatgatcg aggaacggct gaaaacctat gcccacctgt    4020
tcgacgacaa agtgatgaag cagctgaagc ggcgagata caccggctgg ggcaggctga    4080
gccggaagct gatcaacggc atccgggaca agcagtccgg caagacaatc ctggatttcc    4140
tgaagtccga cggcttcgcc aacagaaact tcatgcagct gatccacgac gacagcctga    4200
cctttaaaga ggacatccag aaagcccagg tgtccggcca gggcgatagc ctgcacgagc    4260
acattgccaa tctggccggc agccccgcca ttaagaaggg catcctgcag acagtgaagg    4320
tggtggacga gctcgtgaaa gtgatgggcc ggcacaagcc cgagaacatc gtgatcgaaa    4380
```

```
tggccagaga gaaccagacc acccagaagg gacagaagaa cagccgcgag agaatgaagc    4440
ggatcgaaga gggcatcaaa gagctgggca gccagatcct gaaagaacac cccgtggaaa    4500
acacccagct gcagaacgag aagctgtacc tgtactacct gcagaatggg cgggatatgt    4560
acgtggacca ggaactggac atcaaccggc tgtccgacta cgatgtggac catatcgtgc    4620
ctcagagctt tctgaaggac gactccatcg acaacaaggt gctgaccaga agcgacaaga    4680
accggggcaa gagcgacaac gtgcccctccg aagaggtcgt gaagaagatg aagaactact    4740
ggcggcagct gctgaacgcc aagctgatta cccagagaaa gttcgacaat ctgaccaagg    4800
ccgagagagg cggcctgagc gaactggata aggccggctt catcaagaga cagctggtgg    4860
aaacccggca gatcacaaag cacgtggcac agatcctgga ctcccggatg aacactaagt    4920
acgacgagaa tgacaagctg atccgggaag tgaaagtgat caccctgaag tccaagctgg    4980
tgtccgattt ccggaaggat ttccagtttt acaaagtgcg cgagatcaac aactaccacc    5040
acgcccacga cgcctacctg aacgccgtcg tgggaaccgc cctgatcaaa aagtaccctaa    5100 agctggaaag cgagttcgtg tacggcgact acaaggtgta cgacgtgcgg aagatgatcg    5160
ccaagagcga gcaggaaatc ggcaaggcta ccgccaagta cttcttctac agcaacatca    5220 tgaactttt caagaccgag attaccctgg ccaacgcga gatccggaag cggcctctga    5280
tcgagacaaa cggcgaaacc ggggagatcg tgtgggataa gggccgggat tttgccaccg    5340
tgcggaaagt gctgagcatg ccccaagtga atatcgtgaa aaagaccgag gtgcagacag    5400
gcggcttcag caaagagtct atcctgccca gaggaacag cgataagctg atcgccagaa    5460
agaaggactg ggaccctaag aagtacggcg gcttcgacag ccccaccgtg gcctattctg    5520
tgctggtggt ggccaaagtg gaaaagggca gtccaagaa actgaagagt gtgaaagagc    5580
tgctggggat caccatcatg gaaagaagca gcttcgagaa gaatcccatc gactttctgg    5640
aagccaaggg ctacaaagaa gtgaaaaagg acctgatcat caagctgcct aagtactccc    5700
tgttcgagct ggaaaacggc cggaagagaa tgctggcctc tgccggcgaa ctgcagaagg    5760
gaaacgaact ggccctgccc tccaaatatg tgaacttcct gtacctggcc agccactatg    5820
agaagctgaa gggctccccc gaggataatg agcagaaaca gctgtttgtg gaacagcaca    5880
agcactacct ggacgagatc atcgagcaga tcagcgagtt ctccaagaga gtgatcctgg    5940
ccgacgctaa tctggacaaa gtgctgtccg cctacaacaa gcaccgggat aagcccatca    6000
gagagcaggc cgagaatatc atccacctgt ttaccctgac caatctggga gcccctgccg    6060
ccttcaagta ctttgacacc accatcgacc ggaagaggta caccagcacc aaagaggtgc    6120
tggacgccac cctgatccac cagagcatca ccggcctgta cgagacacgg atcgacctgt    6180
ctcagctggg aggcgacaaa aggccggcgg ccacgaaaaa ggccggccag gcaaaaaaga    6240
aaaagtaaga attcctagag ctcgctgatc agcctcgact gtgccttcta gttgccagcc    6300
atctgttgtt tgcccctccc ccgtgccttc cttgaccctg gaaggtgcca ctcccactgt    6360
cctttcctaa taaaatgagg aaattgcatc gcattgtctg agtaggtgtc attctattct    6420
ggggggtggg gtggggcagg acagcaaggg ggaggattgg gaagagaata gcaggcatgc    6480
tggggagcgg ccgcaggaac ccctagtgat ggagttggcc actccctctc tgcgcgctcg    6540
ctcgctcact gaggccgggc gaccaaaggt cgcccgacgc ccgggctttg cccgggcggc    6600
ctcagtgagc gagcgagcgc gcagctgcct gcagggcgc ctgatgcggt attttctcct    6660
tacgcatctg tgcggtattt cacaccgcat acgtcaaagc aaccatagta cgcgccctgt    6720
agcggcgcat taagcgcggc gggtgtggtg gttacgcgca gcgtgaccgc tacacttgcc    6780
```

```
agcgccctag cgcccgctcc tttcgctttc ttcccttcct ttctcgccac gttcgccggc    6840
tttccccgtc aagctctaaa tcggggggctc cctttagggt tccgatttag tgctttacgg    6900 caccctcgacc ccaaaaaact tgatttgggt gatggttcac gtagtgggcc atcgccctga    6960
tagacggttt ttcgcccttt gacgttggag tccacgttct ttaatagtgg actcttgttc    7020
caaactggaa caacactcaa ccctatctcg gctattctt ttgatttata agggattttg    7080
ccgatttcgg cctattggtt aaaaatgag ctgatttaac aaaaatttaa cgcgaatttt    7140
aacaaaatat taacgtttac aattttatgg tgcactctca gtacaatctg ctctgatgcc    7200
gcatagttaa gccagccccg acacccgcca acccgctg acgcgccctg acgggcttgt    7260
ctgctcccgg catccgctta cagacaagct gtgaccgtct ccgggagctg catgtgtcag    7320
aggttttcac cgtcatcacc gaaacgcgcg agacgaaagg gcctcgtgat acgcctattt    7380
ttataggtta atgtcatgat aataatggtt tcttagacgt caggtggcac ttttcgggga    7440
aatgtgcgcg gaacccctat ttgtttattt ttctaaatac attcaaatat gtatccgctc    7500
atgagacaat aaccctgata aatgcttcaa taatattgaa aaaggaagag tatgagtatt    7560
caacatttcc gtgtcgccct tattcccttt tttgcggcat tttgccttcc tgttttgct    7620 cacccagaaa cgctggtgaa agtaaaagat gctgaagatc agttgggtgc acgagtgggt    7680
tacatcgaac tggatctcaa cagcggtaag atccttgaga gttttcgccc cgaagaacgt    7740
tttccaatga tgagcacttt taaagttctg ctatgtggcg cggtattatc ccgtattgac    7800
gccgggcaag agcaactcgg tcgccgcata cactattctc agaatgactt ggttgagtac    7860
tcaccagtca cagaaaagca tcttacggat ggcatgacag taagagaatt atgcagtgct    7920
gccataacca tgagtgataa cactgcggcc aacttacttc tgacaacgat cggaggaccg    7980
aaggagctaa ccgcttttttt gcacaacatg ggggatcatg taactcgcct tgatcgttgg    8040
gaaccggagc tgaatgaagc cataccaaac gacgagcgtg acaccacgat gcctgtagca    8100
atggcaacaa cgttgcgcaa actattaact ggcgaactac ttactctagc ttcccggcaa    8160
caattaatag actggatgga ggcggataaa gttgcaggac cacttctgcg ctcggccctt    8220
ccggctggct ggtttattgc tgataaatct ggagccggtg agcgtggaag ccgcggtatc    8280
attgcagcac tggggccaga tggtaagccc tcccgtatcg tagttatcta cacgacgggg    8340
agtcaggcaa ctatgatga acgaaataga cagatcgctg agataggtgc ctcactgatt    8400
aagcattggt aactgtcaga ccaagtttac tcatatatac tttagattga tttaaaactt    8460 cattttttaat ttaaaaggat ctaggtgaag atcctttttg ataatctc                8508
```

<210> SEQ ID NO 6
<211> LENGTH: 8508
<212> TYPE: DNA
<213> ORGANISM: Artificial Sequence
<220> FEATURE:
<223> OTHER INFORMATION: Beta4GalNT2-CRISPR/Cas9

<400> SEQUENCE: 6

```
atgaccaaaa tcccttaacg tgagttttcg ttccactgag cgtcagaccc cgtagaaaag     60
atcaaaggat cttcttgaga tcctttttttt ctgcgcgtaa tctgctgctt gcaaacaaaa    120
aaaccaccgc taccagcggt ggtttgtttg ccggatcaag agctaccaac tcttttttccg    180 aaggtaactg gcttcagcag agcgcagata ccaaatactg tccttctagt gtagccgtag    240
ttaggccacc acttcaagaa ctctgtagca ccgcctacat acctcgctct gctaatcctg    300
```

-continued

```
ttaccagtgg ctgctgccag tggcgataag tcgtgtctta ccgggttgga ctcaagacga      360
tagttaccgg ataaggcgca gcggtcgggc tgaacggggg gttcgtgcac acagcccagc      420
ttggagcgaa cgacctacac cgaactgaga tacctacagc gtgagctatg agaaagcgcc      480
acgcttcccg aagggagaaa ggcggacagg tatccggtaa gcggcagggt cggaacagga      540
gagcgcacga gggagcttcc aggggggaaac gcctggtatc tttatagtcc tgtcgggttt     600
cgccacctct gacttgagcg tcgattttttg tgatgctcgt caggggggcg agcctatgg      660 aaaaacgcca gcaacgcggc cttttttacgg ttcctggcct tttgctggcc ttttgctcac     720
atgtgagggc ctatttccca tgattccttc atatttgcat atacgataca aggctgttag      780
agagataatt ggaattaatt tgactgtaaa cacaaagata ttagtacaaa atacgtgacg      840
tagaaagtaa taatttcttg ggtagtttgc agttttaaaa ttatgttttta aaatggacta    900 tcatatgctt accgtaactt gaaagtattt cgatttcttg gctttatata tcttgtggaa     960
aggacgaaac accggtagta ctcacgaaca ctcgttttag agctagaaat agcaagttaa    1020
aataaggcta gtccgttatc aacttgaaaa agtggcaccg agtcggtgct ttttttgtttt    1080 agagctagaa atagcaagtt aaaataaggc tagtccgttt ttagcgcgtg cgccaattct    1140
gcagacaaat ggctctagag gtacccgtta cataacttac ggtaaatggc ccgcctggct    1200
gaccgcccaa cgaccccgc ccattgacgt caatagtaac gccataggg actttccatt      1260 gacgtcaatg ggtggagtat ttacggtaaa ctgcccactt ggcagtacat caagtgtatc    1320
atatgccaag tacgccccct attgacgtca atgacggtaa atggcccgcc tggcattgtg    1380
cccagtacat gaccttatgg gactttccta cttggcagta catctacgta ttagtcatcg    1440
ctattaccat ggtcgaggtg agccccacgt tctgcttcac tctccccatc tcccccccct    1500
ccccaccccc aattttgtat ttatttattt tttaattatt ttgtgcagcg atggggggcgg    1560 gggggggggg ggggcgcgcg ccaggcgggg cggggcgggg cgaggggcgg ggcggggcga    1620
ggcggagagg tgcggcggca gccaatcaga gcggcgcgct ccgaaagttt ccttttatgg    1680
cgaggcggcg gcggcggcgg ccctataaaa agcgaagcgc gcggcgggcg ggagtcgctg    1740
cgacgctgcc ttcgccccgt gccccgctcc gccgccgcct cgcgccgccc gccccggctc    1800
tgactgaccg cgttactccc acaggtgagc gggcgggacg gcccttctcc tccgggctgt    1860
aattagctga gcaagaggta aggggtttaag ggatggttgg ttggtggggt attaatgttt    1920
aattacctgg agcacctgcc tgaaatcact ttttttcagg ttggaccggt gccaccatgg    1980
actataagga ccacgacgga gactacaagg atcatgatat tgattacaaa gacgatgacg    2040
ataagatggc cccaaagaag aagcggaagg tcggtatcca cggagtccca gcagccgaca    2100
agaagtacag catcggcctg gacatcggca ccaactctgt gggctgggcc gtgatcaccg    2160
acgagtacaa ggtgcccagc aagaaattca aggtgctggg caacaccgac cggcacagca    2220
tcaagaagaa cctgatcgga gccctgctgt tcgacagcgg cgaaacagcc gaggccaccc    2280
ggctgaagag aaccgccaga agaagataca ccagacggaa gaaccggatc tgctatctgc    2340
aagagatctt cagcaacgag atggccaagg tggacgacag cttcttccac agactggaag    2400
agtccttcct ggtggaagag gataagaagc acgagcggca ccccatcttc ggcaacatcg    2460
tggacgaggt ggcctaccac gagaagtacc ccaccatcta ccacctgaga aagaaactgg    2520
tggacagcac cgacaaggcc gacctgcggc tgatctatct ggccctggcc cacatgatca    2580
agttccgggg ccacttcctg atcgagggcg acctgaaccc cgacaacagc gacgtggaca    2640
agctgttcat ccagctggtg cagacctaca accagctgtt cgaggaaaac cccatcaacg    2700
```

```
ccagcggcgt ggacgccaag gccatcctgt ctgccagact gagcaagagc agacggctgg    2760
aaaatctgat cgcccagctg cccggcgaga agaagaatgg cctgttcgga aacctgattg    2820
ccctgagcct gggcctgacc cccaacttca agagcaactt cgacctggcc gaggatgcca    2880
aactgcagct gagcaaggac acctacgacg acgacctgga caacctgctg gcccagatcg    2940
gcgaccagta cgccgacctg tttctggccg ccaagaacct gtccgacgcc atcctgctga    3000
gcgacatcct gagagtgaac accgagatca ccaaggcccc cctgagcgcc tctatgatca    3060
agagatacga cgagcaccac caggacctga ccctgctgaa agctctcgtg cggcagcagc    3120
tgcctgagaa gtacaaagag attttcttcg accagagcaa gaacggctac gccggctaca    3180
ttgacggcgg agccagccag gaagagttct acaagttcat caagcccatc ctggaaaaga    3240
tggacggcac cgaggaactg ctcgtgaagc tgaacagaga ggacctgctg cggaagcagc    3300
ggaccttcga caacggcagc atcccccacc agatccacct gggagagctg cacgccattc    3360
tgcggcggca ggaagatttt taccccattc tgaaggacaa ccgggaaaag atcgagaaga    3420
tcctgacctt ccgcatcccc tactacgtgg gccctctggc caggggaaac agcagattcg    3480
cctggatgac cagaaagagc gaggaaacca tcacccctg gaacttcgag gaagtggtgg    3540
acaagggcgc ttccgcccag agcttcatcg agcggatgac caacttcgat aagaacctgc    3600
ccaacgagaa ggtgctgccc aagcacagcc tgctgtacga gtacttcacc gtgtataacg    3660
agctgaccaa agtgaaatac gtgaccgagg gaatgagaaa gcccgccttc ctgagcggcg    3720
agcagaaaaa ggccatcgtg gacctgctgt tcaagaccaa ccggaaagtg accgtgaagc    3780
agctgaaaga ggactacttc aagaaaatcg agtgcttcga ctccgtggaa atctccggcg    3840
tggaagatcg gttcaacgcc tccctgggca taccacga tctgctgaaa attatcaagg    3900
acaaggactt cctggacaat gaggaaaacg aggacattct ggaagatatc gtgctgaccc    3960
tgacactgtt tgaggacaga gagatgatcg aggaacggct gaaaacctat gcccacctgt    4020
tcgacgacaa agtgatgaag cagctgaagc ggcggagata caccggctgg ggcaggctga    4080
gccgaaagct gatcaacggc atccgggaca agcagtccgg caagacaatc ctggatttcc    4140
tgaagtccga cggcttcgcc aacagaaact tcatgcagct gatccacgac gacagcctga    4200
cctttaaaga ggacatccag aaagcccagg tgtccggcca gggcgatagc ctgcacgagc    4260
acattgccaa tctggccggc agccccgcca ttaagaaggg catcctgcag acagtgaagg    4320
tggtggacga gctcgtgaaa gtgatgggcc ggcacaagcc cgagaacatc gtgatcgaaa    4380
tggccagaga gaaccagacc acccagaagg acagaagaa cagccgcgag agaatgaagc    4440
ggatcgaaga gggcatcaaa gagctgggcg ccagatcct gaaagaacac cccgtggaaa    4500
acacccagct gcaaacgag aagctgtacc tgtactacct gcagaatggg cgggatatgt    4560
acgtggacca ggaactggac atcaaccggc tgtccgacta cgatgtggac catatcgtgc    4620
ctcagagctt tctgaaggac gactccatcg acaacaaggt gctgaccaga agcgacaaga    4680 accgggggcaa gagcgacaac gtgcccctccg aagaggtcgt gaagaagatg aagaactact    4740
ggcggcagct gctgaacgcc aagctgatta cccagagaaa gttcgacaat ctgaccaagg    4800
ccgagagagg cggcctgagc gaactggata aggccggctt catcaagaga cagctggtgg    4860
aaacccggca gatcacaaag cacgtggcac agatcctgga ctcccggatg aacactaagt    4920
acgacgagaa tgacaagctg atccgggaag tgaaagtgat caccctgaag tccaagctgg    4980
tgtccgattt ccggaaggat ttccagtttt acaaagtgcg cgagatcaac aactaccacc    5040
```

```
acgcccacga cgcctacctg aacgccgtcg tgggaaccgc cctgatcaaa aagtacccta      5100
agctggaaag cgagttcgtg tacggcgact acaaggtgta cgacgtgcgg aagatgatcg      5160
ccaagagcga gcaggaaatc ggcaaggcta ccgccaagta cttcttctac agcaacatca      5220
tgaactttt caagaccgag attaccctgg ccaacggcga gatccggaag cggcctctga       5280
tcgagacaaa cggcgaaacc ggggagatcg tgtgggataa gggccgggat tttgccaccg      5340
tgcggaaagt gctgagcatg ccccaagtga atatcgtgaa aaagaccgag gtgcagacag      5400
gcggcttcag caaagagtct atcctgccca agaggaacag cgataagctg atcgccagaa      5460
agaaggactg ggaccctaag aagtacgcg gcttcgacag ccccaccgtg cctattctg        5520
tgctggtggt ggccaaagtg gaaaagggca gtccaagaa actgaagagt gtgaaagagc       5580
tgctggggat caccatcatg gaagaagca gcttcgagaa gaatcccatc gactttctgg       5640
aagccaaggg ctacaaagaa gtgaaaaagg acctgatcat caagctgcct aagtactccc      5700
tgttcgagct ggaaaacggc cggaagagaa tgctggcctc tgccggcgaa ctgcagaagg      5760
gaaacgaact ggccctgccc tccaaatatg tgaacttcct gtacctggcc agccactatg      5820
agaagctgaa gggctccccc gaggataatg agcagaaaca gctgtttgtg gaacagcaca      5880
agcactacct ggacgagatc atcgagcaga tcagcgagtt ctccaagaga gtgatcctgg      5940
ccgacgctaa tctggacaaa gtgctgtccg cctacaacaa gcaccgggat aagcccatca      6000
gagagcaggc cgagaatatc atccacctgt ttaccctgac caatctggga gcccctgccg      6060
ccttcaagta ctttgacacc accatcgacc ggaagaggta caccagcacc aaagaggtgc      6120
tggacgccac cctgatccac cagagcatca ccggcctgta cgagacacgg atcgacctgt      6180
ctcagctggg aggcgacaaa aggccggcgg ccacgaaaaa ggccggccag gcaaaaaaga      6240
aaaagtaaga attcctagag ctcgctgatc agcctcgact gtgccttcta gttgccagcc      6300
atctgttgtt tgcccctccc ccgtgccttc cttgaccctg gaaggtgcca ctcccactgt      6360
cctttcctaa taaaatgagg aaattgcatc gcattgtctg agtaggtgtc attctattct      6420
ggggggtggg gtggggcagg acagcaaggg ggaggattgg gaagagaata gcaggcatgc      6480
tggggagcgg ccgcaggaac ccctagtgat ggagttggcc actccctctc tgcgcgctcg      6540
ctcgctcact gaggccgggc gaccaaaggt cgcccgacgc ccgggctttg cccgggcggc      6600
ctcagtgagc gagcgagcgc gcagctgcct gcaggggcgc ctgatgcggt attttctcct      6660
tacgcatctg tgcggtattt cacaccgcat acgtcaaagc aaccatagta cgcgccctgt      6720
agcggcgcat taagcgcggc gggtgtggtg gttacgcgca gcgtgaccgc tacacttgcc      6780
agcgccctag cgcccgctcc tttcgctttc ttcccttcct ttctcgccac gttcgccggc      6840
tttccccgtc aagctctaaa tcgggggctc cctttagggt tccgatttag tgctttacgg      6900
cacctcgacc ccaaaaaact tgatttgggt gatggttcac gtagtgggcc atcgccctga      6960
tagacggttt ttcgcccttt gacgttggag tccacgttct ttaatagtgg actcttgttc      7020
caaactggaa caacactcaa ccctatctcg ggctattctt ttgatttata agggattttg      7080
ccgatttcgg cctattggtt aaaaaatgag ctgatttaac aaaaatttaa cgcgaatttt      7140
aacaaaatat taacgtttac aattttatgg tgcactctca gtacaatctg ctctgatgcc      7200
gcatagttaa gccagccccg acacccgcca acacccgctg acgcgccctg acgggcttgt      7260
ctgctcccgg catccgctta cagacaagct gtgaccgtct ccgggagctg catgtgtcag      7320
aggttttcac cgtcatcacc gaaacgcgcg agacgaaagg gcctcgtgat acgcctattt      7380
ttataggtta atgtcatgat aataatggtt tcttagacgt caggtggcac ttttcgggga      7440
```

```
aatgtgcgcg gaaccccctat tgtttatttt ttctaaatac attcaaatat gtatccgctc    7500
atgagacaat aaccctgata aatgcttcaa taatattgaa aaaggaagag tatgagtatt    7560
caacatttcc gtgtcgccct tattcccttt tttgcggcat tttgccttcc tgttttttgct    7620 cacccagaaa cgctggtgaa agtaaaagat gctgaagatc agttgggtgc acgagtgggt    7680
tacatcgaac tggatctcaa cagcggtaag atccttgaga gttttcgccc cgaagaacgt    7740
tttccaatga tgagcacttt taaagttctg ctatgtggcg cggtattatc ccgtattgac    7800
gccgggcaag agcaactcgg tcgccgcata cactattctc agaatgactt ggttgagtac    7860
tcaccagtca cagaaaagca tcttacggat ggcatgacag taagagaatt atgcagtgct    7920
gccataacca tgagtgataa cactgcggcc aacttacttc tgacaacgat cggaggaccg    7980
aaggagctaa ccgcttttttt gcacaacatg ggggatcatg taactcgcct tgatcgttgg    8040
gaaccggagc tgaatgaagc cataccaaac gacgagcgtg acaccacgat gcctgtagca    8100
atggcaacaa cgttgcgcaa actattaact ggcgaactac ttactctagc ttcccggcaa    8160
caattaatag actggatgga ggcggataaa gttgcaggac cacttctgcg ctcggccctt    8220
ccggctggct ggtttattgc tgataaatct ggagccggtg agcgtggaag ccgcggtatc    8280
attgcagcac tggggccaga tggtaagccc tcccgtatcg tagttatcta cacgacgggg    8340
agtcaggcaa ctatggatga acgaaataga cagatcgctg agataggtgc ctcactgatt    8400
aagcattggt aactgtcaga ccaagtttac tcatatatac tttagattga tttaaaactt    8460
catttttaat ttaaaaggat ctaggtgaag atcctttttg ataatctc                 8508
```

<210> SEQ ID NO 7
<211> LENGTH: 21
<212> TYPE: DNA
<213> ORGANISM: Artificial Sequence
<220> FEATURE:
<223> OTHER INFORMATION: GGTA1-SgRNA+PAM

<400> SEQUENCE: 7
gaaaataatg aatgtcaaag g                                              21

<210> SEQ ID NO 8
<211> LENGTH: 23
<212> TYPE: DNA
<213> ORGANISM: Artificial Sequence
<220> FEATURE:
<223> OTHER INFORMATION: CMAH-SgRNA+PAM

<400> SEQUENCE: 8
gagtaaggta cgtgatctgt tgg                                            23

<210> SEQ ID NO 9
<211> LENGTH: 23
<212> TYPE: DNA
<213> ORGANISM: Artificial Sequence
<220> FEATURE:
<223> OTHER INFORMATION: Beta4GalNT2-SgRNA+PAM

<400> SEQUENCE: 9
ggtagtactc acgaacactc cgg                                            23

<210> SEQ ID NO 10
<211> LENGTH: 25
<212> TYPE: DNA
<213> ORGANISM: Artificial Sequence
<220> FEATURE:

<223> OTHER INFORMATION: GGTA1 forward primer

<400> SEQUENCE: 10
ccttagtatc cttcccaacc cagac                                    25

<210> SEQ ID NO 11
<211> LENGTH: 26
<212> TYPE: DNA
<213> ORGANISM: Artificial Sequence
<220> FEATURE:
<223> OTHER INFORMATION: GGTA1 reserve primer

<400> SEQUENCE: 11
gctttcttta cggtgtcagt gaatcc                                   26

<210> SEQ ID NO 12
<211> LENGTH: 22
<212> TYPE: DNA
<213> ORGANISM: Artificial Sequence
<220> FEATURE:
<223> OTHER INFORMATION: CMAH forward primer

<400> SEQUENCE: 12
cttggaggtg atttgagttg gg                                       22

<210> SEQ ID NO 13
<211> LENGTH: 22
<212> TYPE: DNA
<213> ORGANISM: Artificial Sequence
<220> FEATURE:
<223> OTHER INFORMATION: CMAH reserve primer

<400> SEQUENCE: 13
cattttcttc ggagttgagg gc                                       22

<210> SEQ ID NO 14
<211> LENGTH: 18
<212> TYPE: DNA
<213> ORGANISM: Artificial Sequence
<220> FEATURE:
<223> OTHER INFORMATION: Beta4GalNT2 forward primer

<400> SEQUENCE: 14
cccaaggatc ctgctgcc                                            18

<210> SEQ ID NO 15
<211> LENGTH: 20
<212> TYPE: DNA
<213> ORGANISM: Artificial Sequence
<220> FEATURE:
<223> OTHER INFORMATION: Beta4GalNT2 reserve primer

<400> SEQUENCE: 15
cgccgtgtaa agaaacctcc                                          20

<210> SEQ ID NO 16
<211> LENGTH: 47
<212> TYPE: DNA
<213> ORGANISM: Artificial Sequence
<220> FEATURE:
<223> OTHER INFORMATION: GGTA1 wild type

<400> SEQUENCE: 16
ttttcccagg agaaaataat gaatgtcaaa ggaagagtgg ttctgtc            47

```
<210> SEQ ID NO 17
<211> LENGTH: 48
<212> TYPE: DNA
<213> ORGANISM: Artificial Sequence
<220> FEATURE:
<223> OTHER INFORMATION: GGTA1 knockout

<400> SEQUENCE: 17
ttttcccagg agaaaataat gaatgttcaa aggaagagtg gttctgtc                    48

<210> SEQ ID NO 18
<211> LENGTH: 47
<212> TYPE: DNA
<213> ORGANISM: Artificial Sequence
<220> FEATURE:
<223> OTHER INFORMATION: CMAH wild type

<400> SEQUENCE: 18
aggtccatgc aggcgtgagt aaggtacgtg atctgttgga agacagt                     47

<210> SEQ ID NO 19
<211> LENGTH: 48
<212> TYPE: DNA
<213> ORGANISM: Artificial Sequence
<220> FEATURE:
<223> OTHER INFORMATION: CMAH knockout

<400> SEQUENCE: 19
aggtccatgc aggcgtgagt aaaggtacgt gatctgttgg aagacagt                    48

<210> SEQ ID NO 20
<211> LENGTH: 47
<212> TYPE: DNA
<213> ORGANISM: Artificial Sequence
<220> FEATURE:
<223> OTHER INFORMATION: Beta4GalNT2 wilde type

<400> SEQUENCE: 20
gggtagtact cacgaacact ccggagcatg gtcatgagct tgtgggg                     47

<210> SEQ ID NO 21
<211> LENGTH: 30
<212> TYPE: DNA
<213> ORGANISM: Artificial Sequence
<220> FEATURE:
<223> OTHER INFORMATION: Beta4GalNT2 knockout

<400> SEQUENCE: 21
actccggagc atggtcatga gcttgtgggg                                        30
```